(12) United States Patent
Omohundro et al.

(10) Patent No.: US 10,631,879 B2
(45) Date of Patent: Apr. 28, 2020

(54) DISPOSABLE FLEXIBLE DRIVESHAFT AND METHOD FOR MANUFACTURING DISPOSABLE FLEXIBLE DRIVESHAFTS

(71) Applicant: Med X Composites, LLC, Minden, NV (US)

(72) Inventors: Thomas W. Omohundro, Minden, NV (US); C. Peter Darby, Gardnerville, NV (US)

(73) Assignee: Med X Composites, LLC, Minden, NV (US)

( * ) Notice: Subject to any disclaimer, the term of this patent is extended or adjusted under 35 U.S.C. 154(b) by 16 days.

(21) Appl. No.: 16/156,282

(22) Filed: Oct. 10, 2018

(65) Prior Publication Data

US 2019/0038295 A1  Feb. 7, 2019

Related U.S. Application Data

(63) Continuation-in-part of application No. 15/913,492, filed on Mar. 6, 2018.

(60) Provisional application No. 62/467,876, filed on Mar. 7, 2017.

(51) Int. Cl.
*A61B 17/16* (2006.01)
*A61B 17/00* (2006.01)

(52) U.S. Cl.
CPC ...... *A61B 17/1631* (2013.01); *A61B 17/1633* (2013.01); *A61B 17/1615* (2013.01); *A61B 2017/0023* (2013.01); *A61B 2017/0046* (2013.01); *A61B 2017/00473* (2013.01); *A61B 2017/00477* (2013.01); *A61B 2017/00526* (2013.01)

(58) Field of Classification Search
CPC .................. A61B 17/1631; A61B 17/1633
See application file for complete search history.

(56) References Cited

U.S. PATENT DOCUMENTS

| | | | |
|---|---|---|---|
| 3,011,255 A * | 12/1961 | Washburn | B23K 11/02 228/125 |
| 5,108,411 A | 4/1992 | McKenzie | |
| 5,488,761 A | 2/1996 | Leone | |
| 5,490,860 A | 2/1996 | Middle et al. | |
| 5,849,023 A | 12/1998 | Mericle | |
| 6,332,886 B1 | 12/2001 | Green et al. | |
| 6,443,973 B1 | 9/2002 | Whitman | |
| 7,407,440 B2 | 8/2008 | White | |
| 8,366,559 B2 | 2/2013 | Papenfuss et al. | |
| 8,960,519 B2 | 2/2015 | Whitman et al. | |

(Continued)

*Primary Examiner* — Jessee R Roe
(74) *Attorney, Agent, or Firm* — Taylor IP, P.C.

(57) ABSTRACT

A method of producing a coil for a flexible drive shaft includes: winding a roving into at least one helical groove of a mandrel; coating the roving with an uncured material; heating the coated roving to a curing temperature in the at least one helical groove of the mandrel to cure the uncured material and form a composite roving; and stripping the composite roving from the mandrel. A method of forming a flexible driveshaft for a surgical instrument is also provided and includes: feeding a plurality of flexible coils into a feeder such that each of the plurality of flexible coils are spaced from one another about a rod; rotating the rod to wind the plurality of flexible coils about the rod; and binding the wound plurality of flexible coils and rod together.

20 Claims, 20 Drawing Sheets

(56) References Cited

U.S. PATENT DOCUMENTS

2006/0241630 A1* 10/2006 Brunnett ............ A61B 17/1624
                                                          606/80
2015/0342619 A1   12/2015  Weitzman
2016/0030072 A1    2/2016  Devlin et al.
2016/0310209 A1   10/2016  Parihar et al.
2017/0007272 A1    1/2017  Weitzman et al.

* cited by examiner

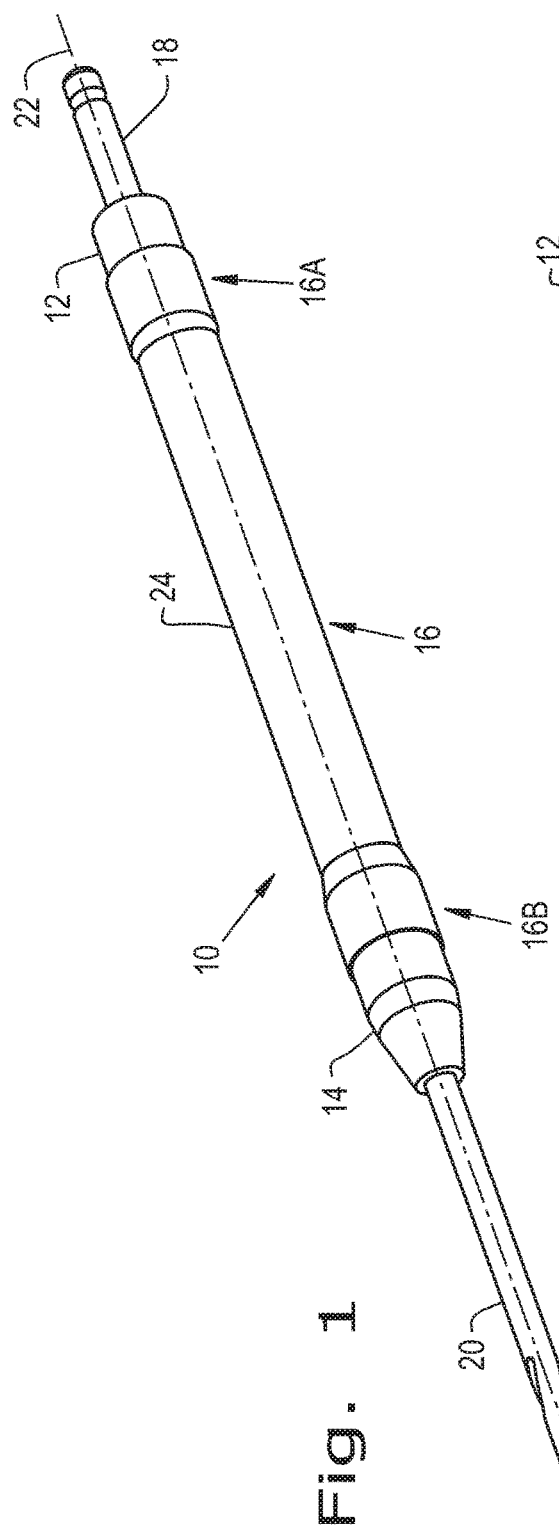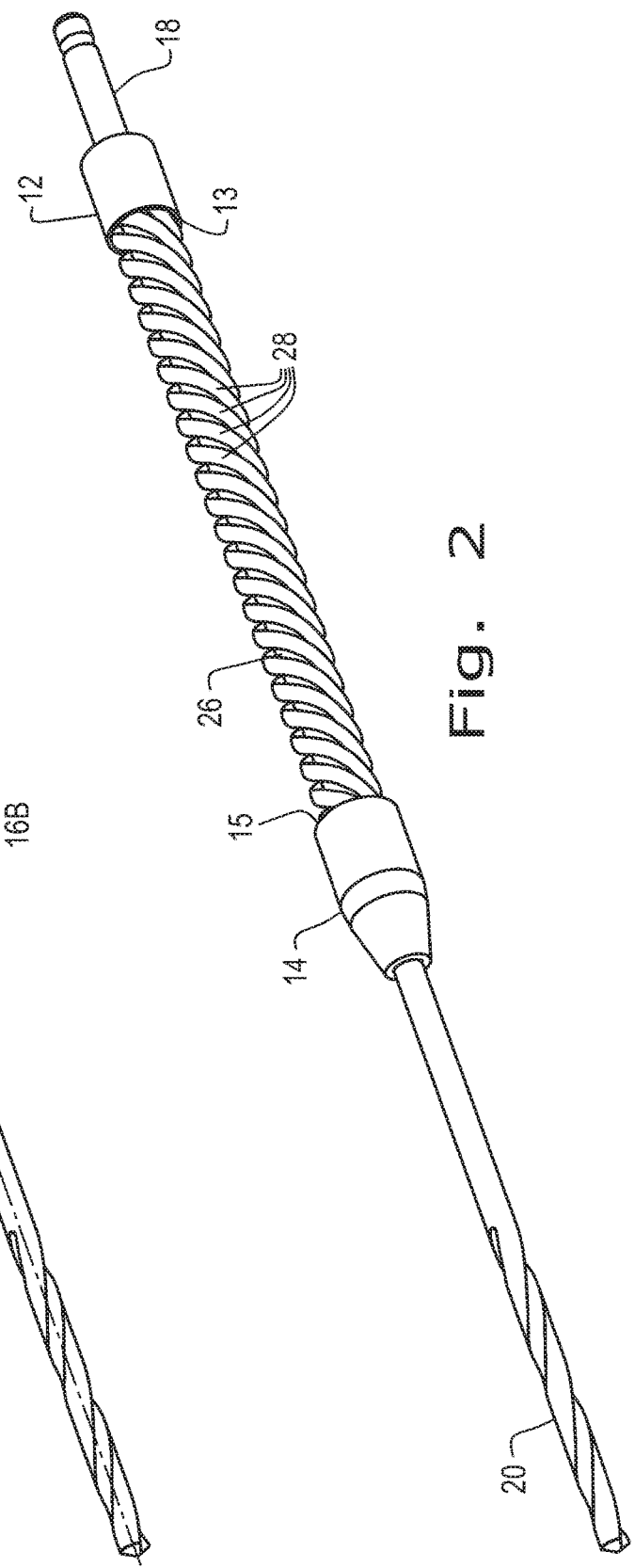

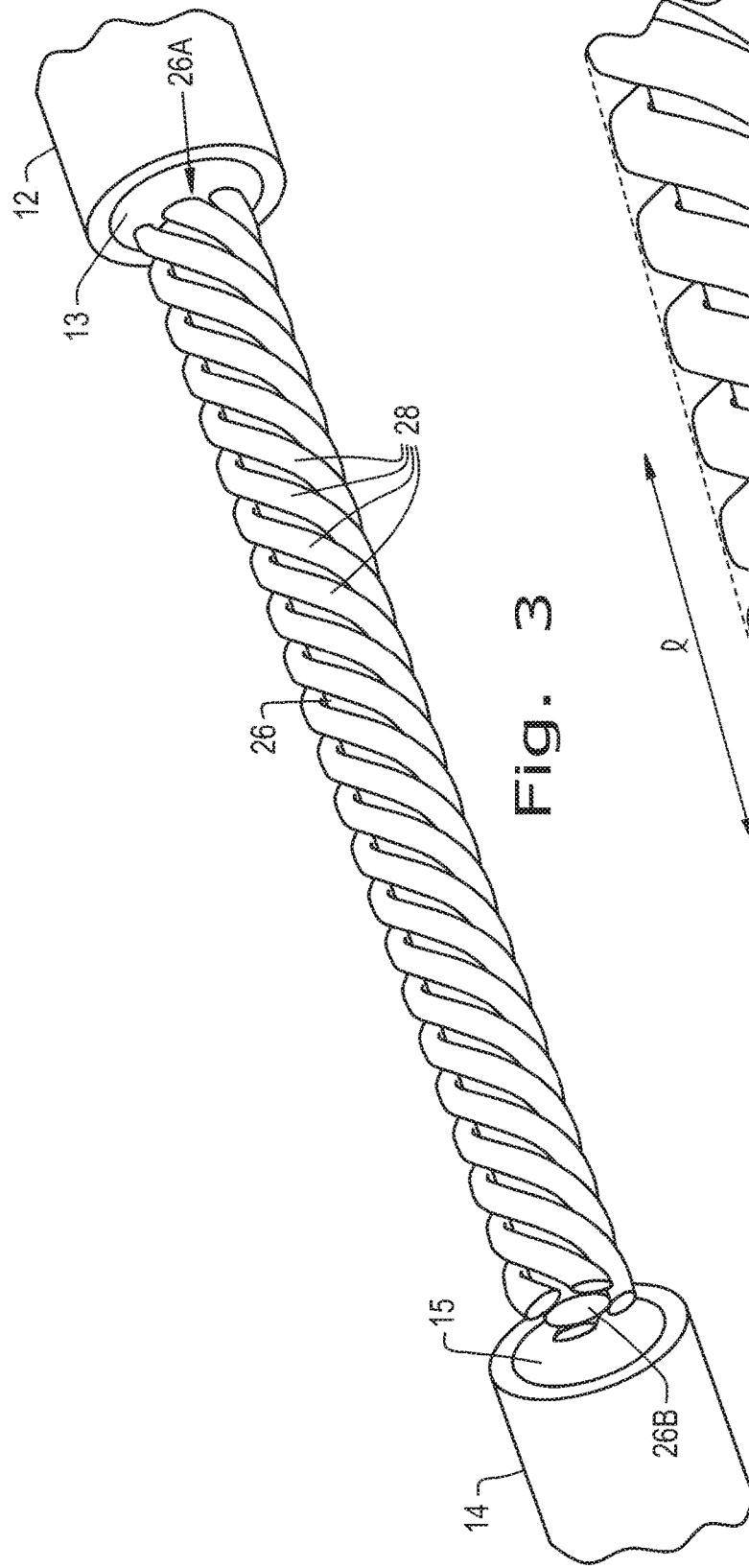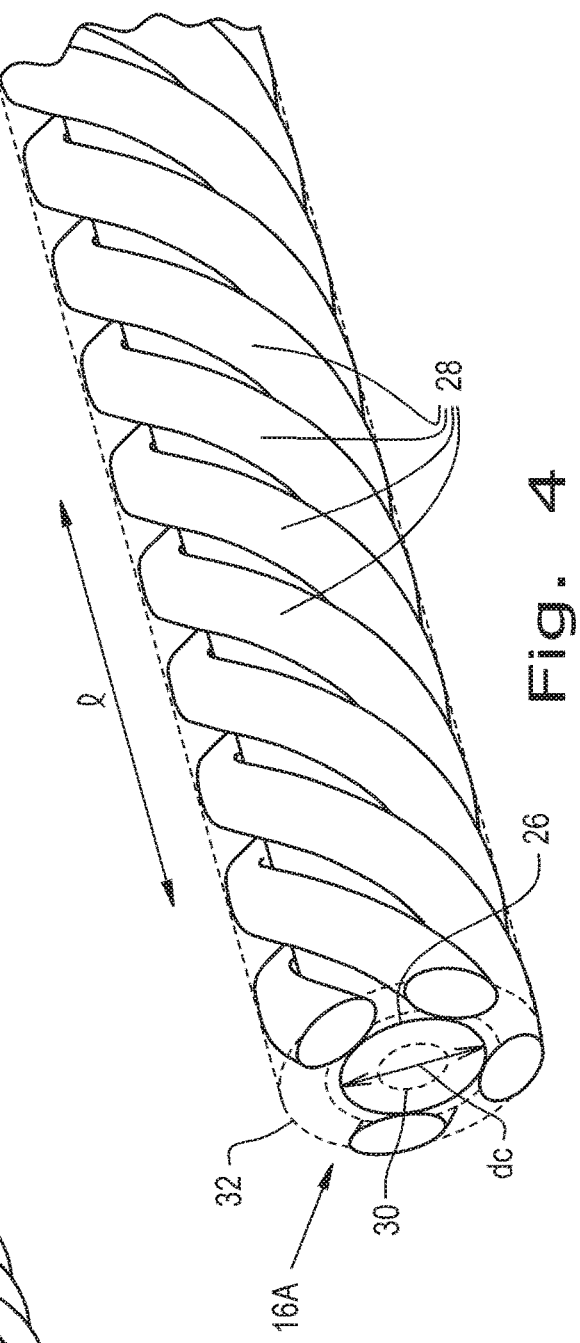

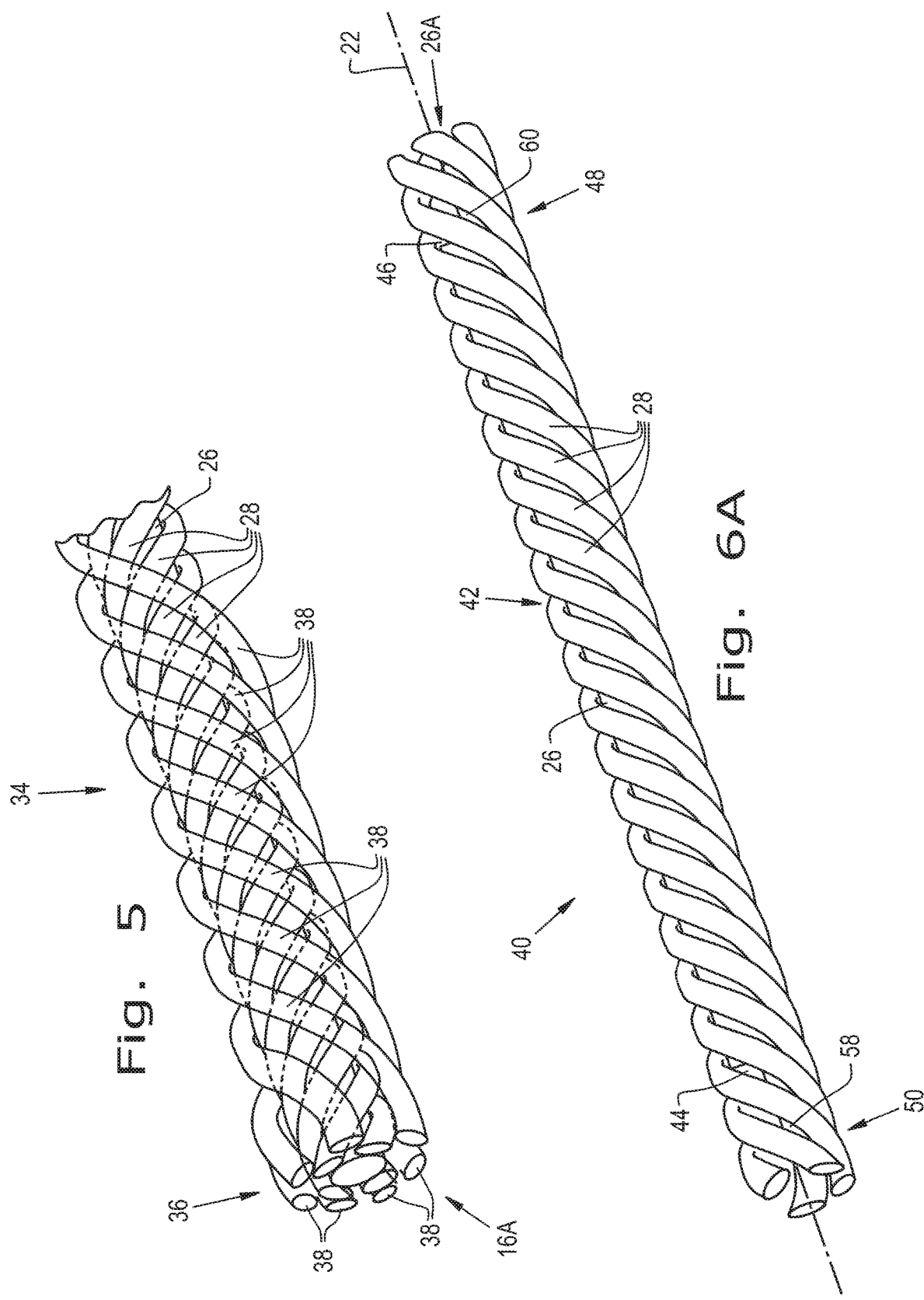

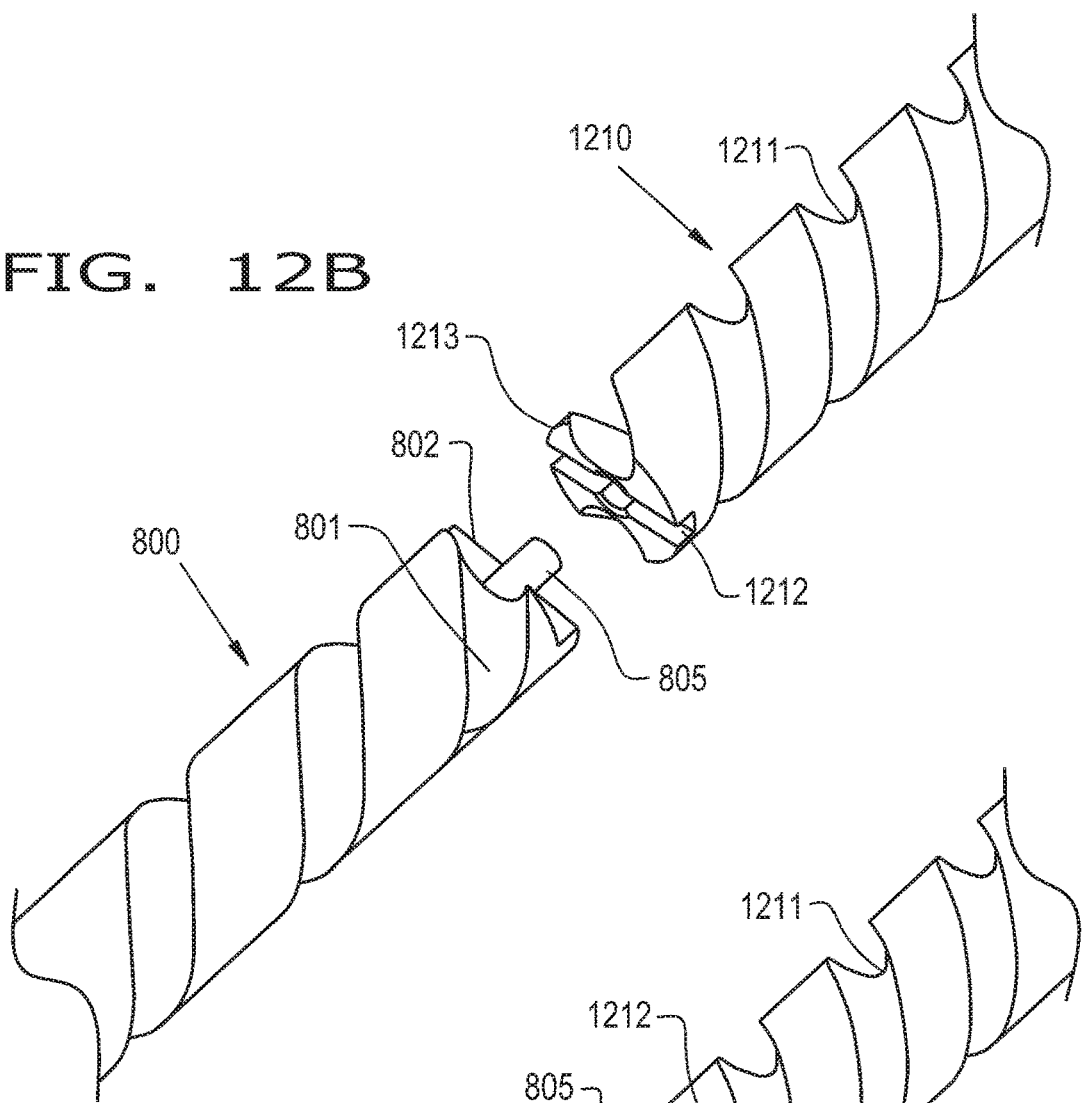
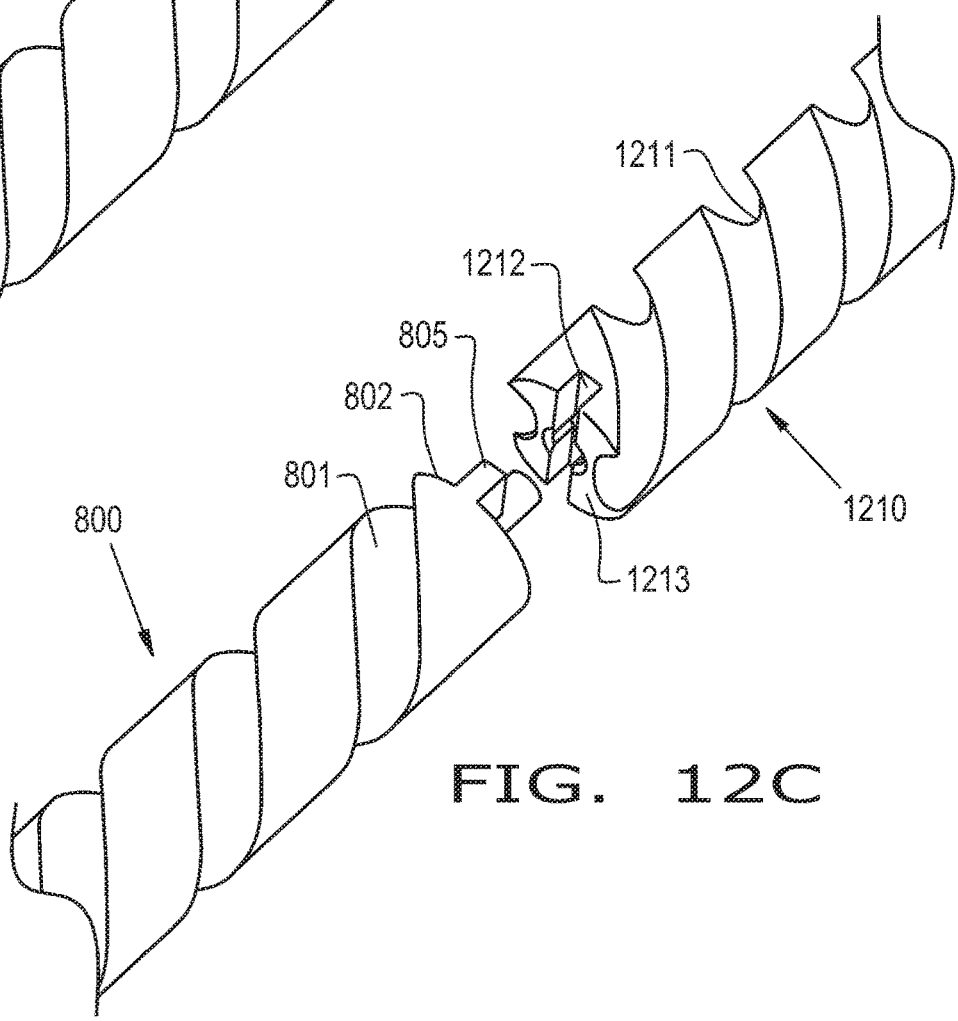

DISPOSABLE FLEXIBLE DRIVESHAFT AND METHOD FOR MANUFACTURING DISPOSABLE FLEXIBLE DRIVESHAFTS

CROSS REFERENCE TO RELATED APPLICATIONS

This application is a continuation-in-part of U.S. patent application Ser. No. 15/913,492, entitled "DISPOSABLE FLEXIBLE DRIVESHAFT," filed Mar. 6, 2018, which is incorporated herein by reference. U.S. patent application Ser. No. 15/913,492 is a non-provisional application based upon U.S. provisional patent application Ser. No. 62/467,876, entitled "SINGLE USE FLEXIBLE DRIVESHAFT", filed Mar. 7, 2017, which is incorporated herein by reference.

BACKGROUND OF THE INVENTION

1. Field of the Invention

The present invention relates to driveshafts, and, more particularly, to a disposable flexible driveshaft as well as methods of manufacturing disposable flexible driveshafts.

2. Description of the Related Art

In surgical operations, it is often advantageous to use a surgical instrument with a flexible shaft, especially when the pathway from the power source to the driven part is obstructed. The flexible shaft circumvents the obstruction while still providing the necessary transmission of force between two components of a surgical instrument. The transmission of force includes both rotary torque and axial force; yet, the primary function of a flexible shaft is to transmit rotary motion in a curvilinear manner. Generally, flexible shafts include a deformable, rotating shaft and a pair of end fittings for respectively attaching the power source and the driven tool of the surgical instrument. For example, a flexible shaft may connect a drill to the tool head for the drilling or reaming of curved bones.

It is well known in the art to use wound springs over a central drive core or a hollow core to form flexible shafts. U.S. Pat. No. 5,108,411 discloses a catheter with a flexible shaft that has an internal drive cable for rotating a work element at the distal end of the catheter. However, such prior art designs which incorporate wound metal springs suffer from sanitation and reusability issues. Predominantly, cleaning and sterilization of the springs is taxingly laborious as blood and debris often becomes lodged within the windings of the springs. Subordinately, spring designs also suffer from unwinding or performance loss as they are rotated in the reverse direction. In order to combat the issues of unwinding, many spring designs incorporated a second, subsidiary spring, which was wound in the opposite direction and disposed within the primary spring. Although the issues of unwinding were waned, the sanitation concerns escalated as the disposition of the subsidiary spring within the primary spring rendered cleaning effectively unreasonable.

As an alternative to the coil spring design, a metallic tubing, wire, or rod may be used to form the flexible driveshaft. It is also known to incorporate a helix structure to ensure the requisite axial flexibility and torsional rigidity of the shaft. Some prior art designs use super-elastic metals, such as U.S. Pat. No. 5,488,761, and U.S. Pat. No. 7,407,440 which uses a nitinol (nickel-titanium) tubing as the body of its shaft. These devices overcome some of the pitfalls of the coil spring design with respect to sanitation and reusability. However, because the prior art metallic tubing, wire, or rod designs are expensive to manufacture they must be reused in order to be cost effective. Therefore, the cost of re-sterilization at the work site or hospital cannot be avoided.

One option to avoid the costs of sterilizing driveshafts between operations is to use a disposable flexible driveshaft, but known manufacturing techniques for producing such driveshafts are relatively expensive and time-consuming.

What is needed in the art is a method for producing flexible driveshafts that is cost-effective and can rapidly produce such flexible driveshafts.

SUMMARY OF THE INVENTION

The present invention provides a flexible driveshaft and associated methods for producing the flexible driveshaft that allow economic manufacturing of the flexible driveshaft.

In some exemplary embodiments described herein, a method of producing a coil for a flexible drive shaft is provided. The method includes: winding a roving into at least one helical groove of a mandrel; coating the roving with an uncured material; heating the coated roving to a curing temperature in the at least one helical groove of the mandrel to cure the uncured material and form a composite roving; and stripping the composite roving from the mandrel.

In some exemplary embodiments described herein, a method of forming a flexible driveshaft for a surgical instrument is provided. The method includes: feeding a plurality of flexible coils into a feeder such that each of the plurality of flexible coils are spaced from one another about a rod; rotating the rod to wind the plurality of flexible coils about the rod; and binding the wound plurality of flexible coils and rod together.

An advantage of the present invention is that flexible driveshafts can be cost effectively produced.

Another advantage of the present invention is that flexible driveshafts can be rapidly manufactured to meet customer demand.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 1 is a perspective view of an embodiment of a flexible driveshaft, coupled to a tool of a surgical instrument, according to an embodiment of the present invention;

FIG. 2 is a perspective view illustrating the flexible driveshaft of FIG. 1 with the absence of the sleeve covering the flexible shaft, according to an embodiment of the present invention;

FIG. 3 is a perspective view illustrating the core and coils of the flexible shaft of FIG. 1, to be coupled to the proximal and distal couplers, according to an embodiment of the present invention;

FIG. 4 is a perspective view of an end of the flexible shaft of FIG. 3, with an optional polymer resin, according to an embodiment of the present invention;

FIG. 5 is a perspective view of an end of the flexible shaft of FIG. 3, with an additional layer of coils spirally-arranged around the core, according to an embodiment of the present invention; and FIG. 6A is a perspective view of a flexible driveshaft, according to another embodiment of the present invention;

FIG. 12B is a perspective view of the mandrel illustrated in FIG. 8 next to an additional mandrel illustrated in FIG. 12A to illustrate an exemplary way of coupling the mandrels to one another;

FIG. 12C is another perspective view of the mandrels illustrated in FIG. 12B after the mandrels have been rotated relative to their position illustrated in FIG. 12B;

Corresponding reference characters indicate corresponding parts throughout the several views. The exemplification set out herein illustrates an embodiment of the invention, in one form, and such exemplification is not to be construed as limiting the scope of the invention in any manner.

DETAILED DESCRIPTION OF THE INVENTION

Figure 6B:
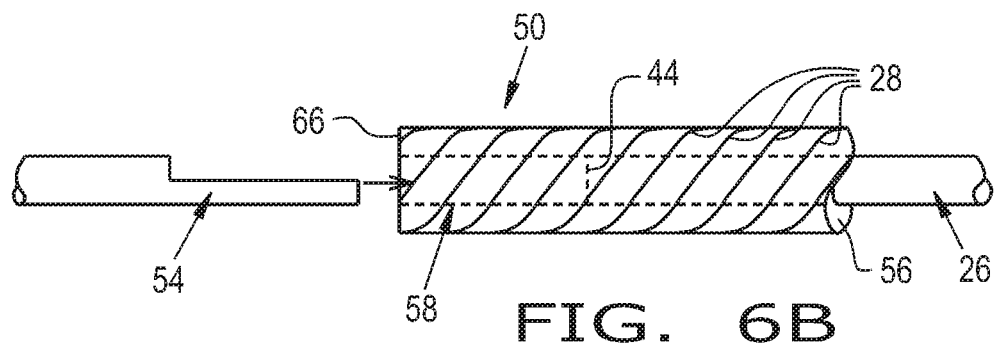
FIG. 6B is a perspective view of a distal end of the flexible driveshaft of FIG. 6A, according to an embodiment of the present invention.

The terms "proximal" and "distal" are used principally throughout this specification for convenience; but it is to be understood that these terms are not intended to be limiting. Thus "proximal" in this specification refers to the feature of the apparatus closest to the operator during use, and "distal" refers to the end of the apparatus farthest from the operator during use.

Referring now to the drawings, and more particularly to FIG. 1, there is shown a flexible driveshaft 10 according to an embodiment of the present invention. The flexible driveshaft 10 includes a proximal coupler 12, a distal coupler 14, and a flexible shaft 16 therebetween. The flexible driveshaft 10 facilitates the drilling of holes in difficult-to-access areas, and it may be manufactured inexpensively enough to be disposable after a single or relatively few uses. The flexible driveshaft 10 may be incorporated as either an element of a one-piece disposable device, or a disposable component of a modular assembly.

For example, the proximal coupler 12, the distal coupler 14 and the flexible shaft 16 may be separate components of the flexible driveshaft 10 of a modular assembly, according to one embodiment of the present invention. In an embodiment of the present invention, the proximal coupler 12 and distal coupler 14 are manufactured from metal, plastic or a composite, and the proximal coupler 12 and distal coupler 14 are removably-connected to the flexible shaft 16 (i.e., to a proximal end 16A and a distal end 16B, respectively, of the flexible shaft 16) such that the flexible shaft 16 is disposable after a single or relatively few uses. Alternatively, the proximal coupler 12 and the distal coupler 14 may be integral, inseparable components of the flexible shaft 16, such that the flexible driveshaft 10 forms a one-piece unit that is disposable after a single or relatively few uses, according to another embodiment of the present invention. In an embodiment of the present invention, the proximal coupler 12 and the distal coupler 14 are each formed of a molded adhesive that are inseparably connected (e.g., bonded) to the flexible shaft 16 (i.e., to the proximal end 16A and the distal end 16B, respectively, of the flexible shaft 16) such that the flexible driveshaft 10 is disposable. Other embodiments of disposable flexible driveshafts and disposable flexible shafts having no couplers are described further below in conjunction with FIGS. 6A-6E.

The proximal and distal couplers 12, 14 attach respective components of a surgical instrument, or components of other types of tools. By way of an exemplary embodiment, the proximal and distal couplers 12, 14 are shown respectively to be in the form of a drive coupler and cutting tool collet. The couplers 12, 14 respectively attach to a power drive attachment 18 and a surgical cutter 20 of a surgical instrument. The power drive attachment 18 is configured to attach to a power source (not shown) which will rotate the flexible shaft 16 and likewise the surgical cutter 20 in order to facilitate the drilling of a bone. The power drive attachment 18 may connect to a motor, a drill, or a handle. The surgical cutter 20 is shown to be a drill bit, but it may be in the form of various interchangeable tools including a reaming head, a screw, a pump, or any other desired orthopedic tool. The proximal and distal couplers 12, 14 can be made of any metal, composite plastic, or adhesive suitable for use with surgical instruments and need not be formed as separate elements, but rather may be formed integrally with the proximal end 16A and the distal end 16B, respectively, of the flexible shaft 16.

Referring now to FIGS. 1-2 collectively, there is shown the flexible shaft 16 which includes the proximal end 16A, the distal end 16B, and a longitudinal axis 22, according to an embodiment of the present invention. The proximal and distal ends 16A, 16B of the flexible shaft 16 connect respectively to the proximal and distal couplers 12, 14 via any known means in the art, including adhesives and/or fasteners. The flexible shaft 16 further includes a sleeve 24, a core 26, and a plurality of coils 28 that are wrapped around the core 26. In one embodiment, the plurality of coils 28 are formed about the core 26 in a counterclockwise direction when the core 26 is viewed from the proximal end 16A, for when the power drive attachment 18 is configured to rotate the flexible shaft 16 in a clockwise direction for proper operation of the tool 20, and the plurality of coils 28 are formed about the core 26 in a clockwise direction when the core 26 is viewed from the proximal end 16A, for when the power drive attachment 18 is configured to rotate the flexible shaft 16 in a counterclockwise direction for proper operation of the tool 20.

The sleeve 24 covers and protects the core 26 and coils 28 of the flexible shaft 16. The sleeve 24 also provides a measure of stiffness such that the when the flexible driveshaft 10 is rotated in the reverse direction it does not succumb to the pitfalls of unwinding or performance loss. In the present embodiment, the sleeve 24 is manufactured of a thin plastic material such that it can be shrink-fit onto the flexible shaft 16. However, the sleeve 24 may be made of any suitable plastic, metal, or composite material, and may be affixed to the couplers 12, 14 by adhesives and/or fasteners. The sleeve 24 may directly abut against the couplers 12, 14, or the sleeve 24 may extend over and onto a respective portion of the couplers 12, 14.

Referring now to FIGS. 2-5 collectively, there is shown in more detail core 26 and the coils 28 which are arranged around the core 26, according to an embodiment of the present invention. The core 26 of the flexible shaft 16 is housed within the sleeve 24, and the respective ends 26A, 26B of the core 26 connect to the proximal coupler 12 and the distal coupler 14. The couplers 12, 14 may include mating bores 13, 15 such that the ends 26A, 26B of the core 26 fit therein. The core 26 in the present embodiment is made from a nylon rod, which is lightweight and cost effective to manufacture. However, the core 26 may be made of any suitable plastic, metal, or composite material that enables the flexible shaft 16 to be cost effectively manufactured. The core 26 may be a solid member or optionally a cannulated member (e.g., including a through-hole 30 coincident with the longitudinal axis 22 of the flexible shaft 16, formed to facilitate a pathway for removal of any material dislodged by the tool (e.g., bone or tissue dislodge by the cutter 20, or by any other orthopedic tool, such as a reaming head)).

In one embodiment, the coils 28 are formed of a fiber-reinforced plastic composite, such as continuous fiberglass-reinforced epoxy resin composite helixes. Alternatively, the coils 28 are formed of other commercial reinforcing fibers, resin matrix materials, or metal wire such as stainless steel or plastic-coated carbon steel. The coils 28 may be arranged about the core 26. The scope of the invention covers coils that are separated from one another and coils embedded in a resin. In another embodiment, the fiber-reinforced plastic composite may be molded to form the coils 28. The coils 28 may also be referred to as a roving, such as a multi-strand fiberglass roving. The coils 28 may also be formed of fibers, for example, glass fibers, carbon fibers, or aramid fibers, that are spirally-arranged about the core 26. As mentioned above, the coils 28 may optionally be embedded in a polymer matrix such as an epoxy resin, an ester, a polyimide, a polypropylene, or any other known material in the art. For example, and as illustrated in FIG. 4, the coils 28 are embedded in a polymer matrix 32, according to an embodiment of the present invention. In one embodiment of the present invention, the coils 28 are spiral-formed fiberglass roving embedded in an epoxy resin.

In one embodiment, the angular orientation of the coils 28 relative to the longitudinal axis 22 of the flexible shaft 16 is approximately 45°, however the scope of the present invention covers the coils 28 having any helix angle with respect to the longitudinal axis 22. In one embodiment of the invention, and as illustrated by FIG. 4, a distance 1 between the same circumferential position of consecutive locations of a single coil (i.e., the helical pitch) is in the range of 18 to 25 mm for the flexible shaft 16 having an outside diameter of 7.5 mm, however the scope of the present invention covers other helical pitches with the same or with different shaft diameters.

FIGS. 2-4 show four coils arranged in a single layer (i.e., a quadruple helix), according to one embodiment of the invention; however, there may be less or more coils arranged around the core 26 according to other embodiments of the invention.

Additionally, there may be multiple layers of coils 28 wrapped around the core 26. For example, FIG. 5 shows the core 26 and two layers of coils 34, 36 which are spirally-arranged (i.e., spiral-formed) around the core 26, according to another embodiment of the present invention. In this embodiment, the flexible shaft 16 (FIG. 1) includes the core 26, a first layer 34 of coils 28 formed from four coils, and a second layer 36 of coils. In one embodiment, the number of coils 38 of the second layer 36 is selected such that the circumferential distance between adjacent coils 38 of the second layer 36 are approximately equal to the circumferential distance between adjacent coils 28 of the first layer 34. For illustration purposes only, the second layer 36 is formed from seven coils. Only a portion of the second layer 36 of coils 38 is shown for ease of illustration. For conventional operation of the flexible driveshaft 16 (i.e., clockwise rotation when viewed from the proximal end 16A), the first layer 34 of coils 28 are wrapped around the core 26 in a clockwise sense when the core 26 is viewed from a perspective of the proximal end 16A (also referred to as a right-hand rotation of the coils or right-handedness), and the second layer 36 of coils 38 are wrapped around the core 26 in a counterclockwise sense when the core 26 is viewed from the perspective of the proximal end 16A (also referred to as left-hand rotation of the coils or left handedness). However, the scope of the present invention covers any number of layers, any number of individual coils forming each of the respective layers, and any combination of handedness of the respective layers.

In one embodiment of the present embodiment, the coils 28 are adhesively bonded at each end to the couplers 12, 14 and to each other. However, in another embodiment of the present invention, the coils 28 may be secured to the couplers 12, 14 by fasteners. The arrangement of the coils 28 wrapped around the core 26 creates a desired balance of the lateral stiffness and torsional strength sufficient for the flexible shaft 16 to push and rotate a tool, such as the surgical cutter 20, when the flexible driveshaft 10 is bent.

FIG. 6A shows a flexible driveshaft 40 according to an embodiment of the present invention. The flexible driveshaft 40 includes a flexible shaft 42 having a longitudinal axis 22, a core 26 having a first end 44 and a second end 46, and a plurality of coils 28 spirally-arranged around the core 26 in at least one layer. The plurality of fibers 28 may be arranged as one or more cylindrical layers. The core and the cylindrical layers are arranged concentrically about the longitudinal axis 22. The flexible driveshaft 40 is similar to the flexible driveshaft 10 in that the flexible driveshaft 40 facilitates the drilling of holes in difficult-to-access areas, and it may be manufactured inexpensively enough to be disposable after a single or relatively few uses.

However, in contrast to the flexible driveshaft 10, the flexible driveshaft 40 does not include proximal and distal couplers. The flexible shaft 42 of the flexible driveshaft 40 includes a proximal end 48 and a distal end 50, each configured to couple to respective components of an instrument or tool, such as surgical tools and power drive attachments, via core recesses 58, 60. For example, in one embodiment of the present invention, the proximal end 48 is configured as a drive coupler for coupling with a driver, such as a power drive attachment 52 (FIG. 6C), and the distal end 50 is configured as a tool collet for coupling with a tool, such as a drill bit 54 (FIG. 6B).

Figure 6C:
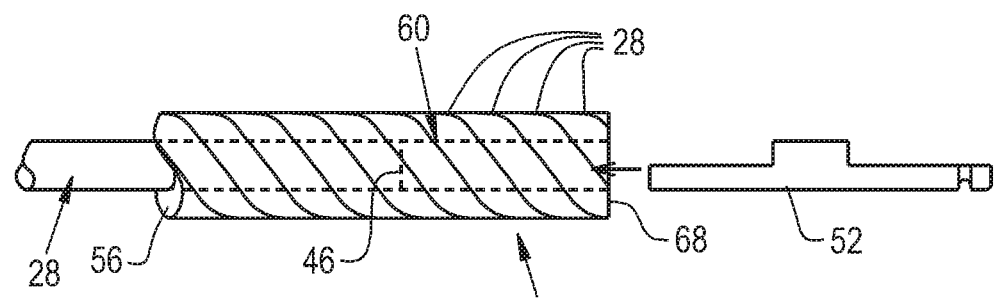
FIG. 6C is a perspective view of a proximal end of the flexible driveshaft of FIG. 6A, according to an embodiment of the present invention.

FIG. 6B and FIG. 6C show the distal end 50 of the flexible shaft 42 and the proximal end 48 of the flexible shaft 42, according to an embodiment of the present invention. As illustrated by FIG. 6B, each coil of the plurality of coils 28 formed of a fiber-reinforced plastic composite 56 or optionally embedded in a polymer resin 56 at the distal end 50 extend beyond the first end 44 of the core 26, thereby forming the distal end core recess 58. Similarly, as illustrated by FIG. 6C, each coil of the plurality of coils 28 formed of the fiber-reinforced plastic composite 56 or optionally embedded in the polymer resin 56 at the proximal end 48 extend beyond the second end 46 of the core 26, thereby forming the proximal end core recess 60. The proximal and distal end core recesses 60, 58 of the proximal and distal ends 48, 50 of the flexible shaft 42 are configured to couple to respective components of a tool, such as a surgical instrument.

Figure 6D:
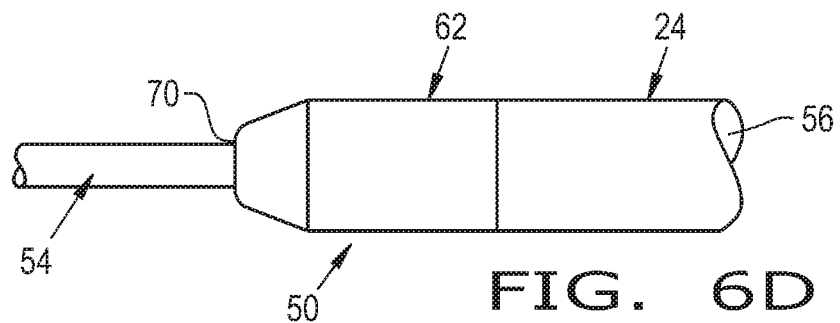
FIG. 6D is a perspective view of the distal end of the flexible driveshaft of FIG. 6B, with an adhesive end coupled to a surgical tool, according to an embodiment of the present invention.
Figure 6E:
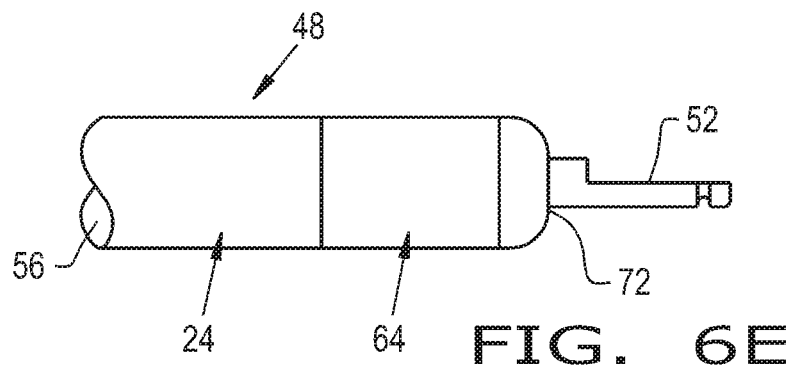
FIG. 6E is a perspective view of the proximal end of the flexible driveshaft of FIG. 6C, with an adhesive end coupled to a drive attachment, according to an embodiment of the present invention.
Figure 7:
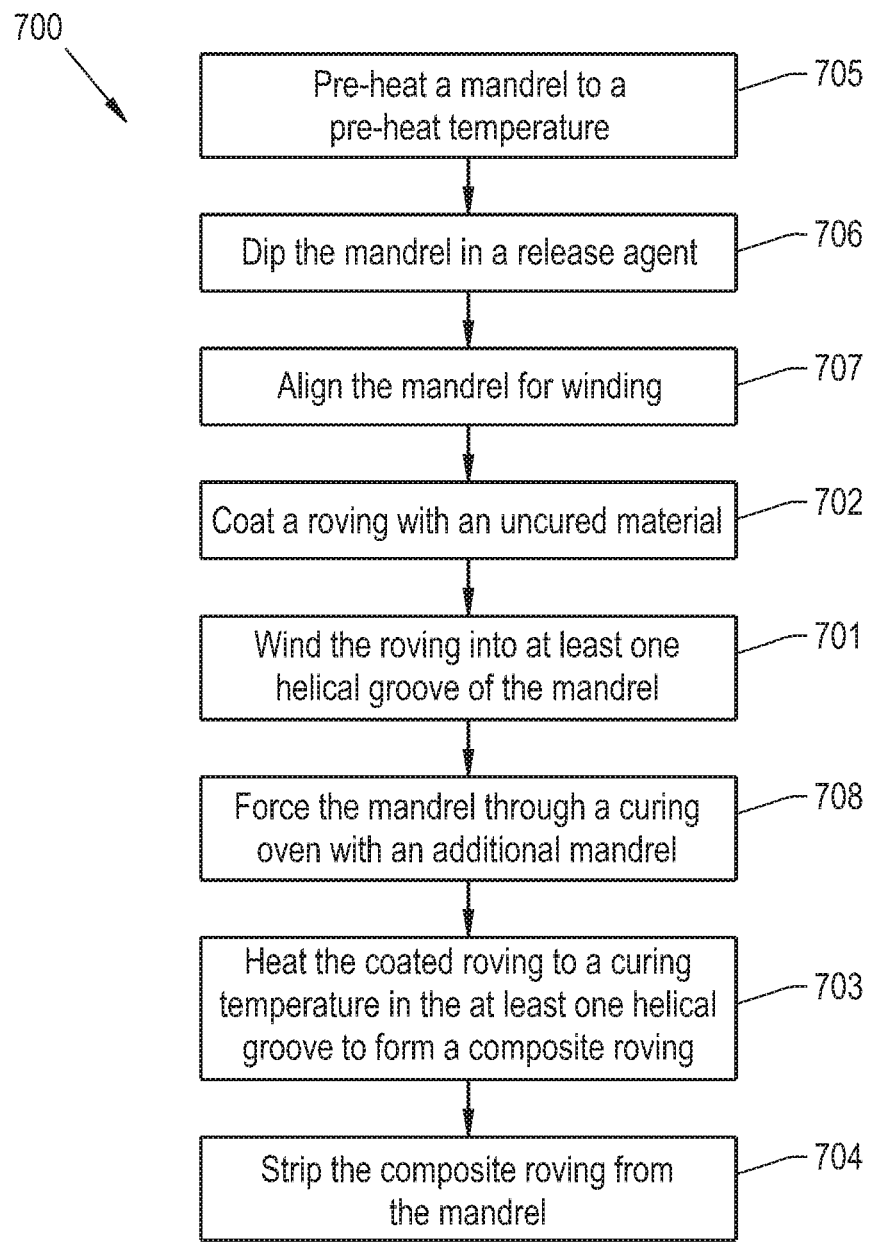
FIG. 7 is a flow chart illustrating an exemplary embodiment of a method of producing a coil for a flexible drive shaft in accordance with the present invention.

FIGS. 6D and 6E show the distal end 50 of the flexible shaft 42 and the proximal end 48 of the flexible shaft 42, as illustrated in FIGS. 6B and 6C respectively, according to another embodiment of the present invention. As illustrated by FIG. 6D, the distal end 50 includes a distal molded or cast adhesive end 62 formed either around the plurality of coils 28 at the distal end 50 that extend beyond the first end 44 of the core 26 that form the core recess 58, or bonded with a first end 66 of the plurality of coils 28. Furthermore, and as illustrated by FIG. 6E, the proximal end 48 includes a proximal molded or cast adhesive end 64 formed either around the plurality of coils 28 at the proximal end 48 that extend beyond the second end 46 of the core 26 that form the core recess 60, or bonded with a second end 68 of the plurality of coils 28. In one embodiment of the present invention, the molded or cast adhesive ends 62, 64 are formed as inseparably components completely integrated with the distal and proximal ends 50, 48. In another embodiment of the invention, the molded or cast adhesive ends 62, 64 include respective openings 70, 72 configured to receive respective components of the tool for coupling the components to the respective core recesses 58, 60. Although FIGS. 6D and 6E show the flexible shaft 42 having a sleeve 24 which either abuts against the molded or cast adhesive ends 62, 64 or covers at least a portion of the molded or cast adhesive ends 62, 64, the scope of the present invention covers the FIGS. 6D and 6E embodiments without the sleeve 24, and the FIGS. 6B and 6C embodiments with a sleeve 24 covering at least a portion of the flexible shaft 42.

As illustrated in FIGS. 6A-6E, the coils 28 forming the core recesses 58, 60 are directly coupled to respective components of a tool when such components are inserted into the respective core recesses 58, 60, with or without the molded or cast adhesive ends 62, 64, thereby coupling the flexible driveshaft 40 directly to the power drive attachment 52 and the tool 54 without the use of separate, non-integrated couplers.

In another embodiment of the invention, and referring to FIGS. 6A-6E, a flexible shaft assembly is the flexible shaft 42 without the core 26. The flexible shaft assembly includes the plurality of coils 28 spirally-arranged (e.g., arranged as helixes) in at least one layer about the longitudinal axis 22. In this embodiment, the plurality of coils 28 form a hollow flexible shaft (i.e., said flexible driveshaft 40 without the core 26).

The distal and proximal ends 50, 48 are configured to permanently bond with, or removeable-couple to, a respective component of a tool, such as a shank of a drill, a ream, an abrading tool, a screw driving bit, a collet with the capability to use interchangeable tools or components of tools, or a coupling to attach a pump (not shown). For example, the proximal and distal ends 48, 50 may be configured to permanently bond with a respective component of a tool by use of an adhesive, a fastener, or a weld.

In another embodiment, the proximal and distal ends 48, 50 of the flexible shaft assembly include a proximal adhesive end 64 attached to the proximal end 48 and a distal adhesive end 62 attached to the distal end 50. Although the adhesive ends 62, 64 are configured to removably-couple to respective components of a tool, such as a driver 52 or other components 54 of a tool, via collet-like-formed adhesive ends, for example, the scope of the present invention covers adhesive ends 62, 64 configured to permanently bond with respective components of a tool. In one embodiment, the driver 52 may be any standard stainless steel quick connect or stainless-steel rod with a quick connect shape cast or molded around the rod bonded to the coils 28 at the proximal end 48 and/or bonded to the proximal adhesive end 64. In one embodiment, the adhesive ends 62, 64 are molded or cast.

In other embodiments of the present invention, the dimensions and material of the core 26 and the coils 28 of the flexible driveshaft 10 and the dimensions and material of the core 26 and the coils 28 of the flexible driveshaft 40 are configured to support a compression load, supply up to 9 N-m of torque, and to support up to 90 degrees of bend as measured with respect to the longitudinal axis 22.

Referring now to FIGS. 7-17, an exemplary embodiment of a method of producing a coil, such as one or more coils 28, for a flexible driveshaft, such as flexible driveshafts 10 and 40, is illustrated. Referring specifically to the flow chart of FIG. 7, it can be seen that the method 700 includes winding 701 a roving 1401 (first illustrated in FIG. 14) into at least one helical groove 801 of a mandrel 800, which is first illustrated in FIG. 8. Before, during, or after winding 701, the roving 1401 is coated 702 with an uncured material. The coated roving 1401 is heated 703 to a curing temperature in the at least one helical groove 801 of the mandrel 800 to cure the uncured material and form a composite roving 1601, which is first illustrated in FIG. 16. The composite roving 1601 is then stripped 704 from the mandrel 800. In some embodiments, the mandrel 800 is pre-heated 705 to a pre-heat temperature and/or dipped 706 in a release agent prior to winding 701 the roving 1401 into the at least one helical groove 801. In some embodiments, the mandrel 800 is aligned 707 for winding. In some embodiments, an additional mandrel 1210 (first illustrated in FIG. 12A) forces 708 the mandrel 800 through a curing oven 1503 (first illustrated in FIG. 14) during heating 703. The method 700 is described in further detail herein with reference to FIGS. 8-17.

Figure 8:
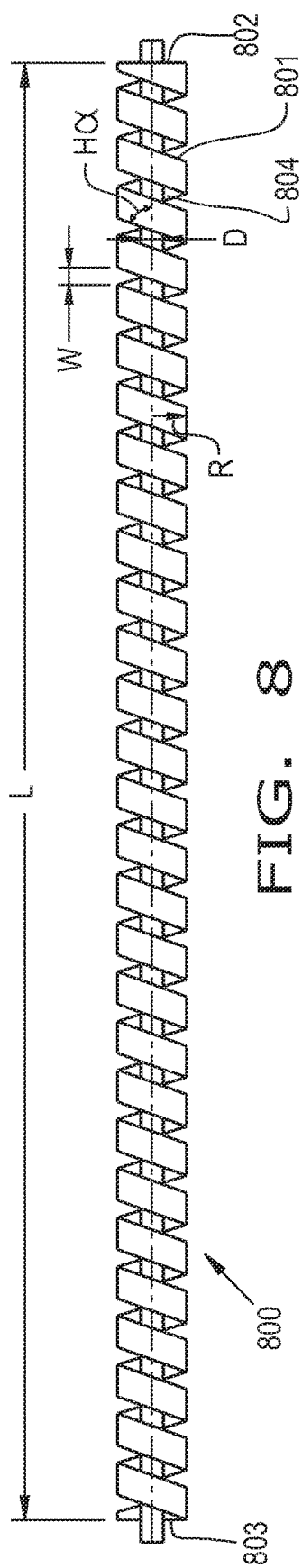
FIG. 8 is a perspective view of an exemplary embodiment of a mandrel that may be used in the method illustrated in FIG. 7.
Figure 9:
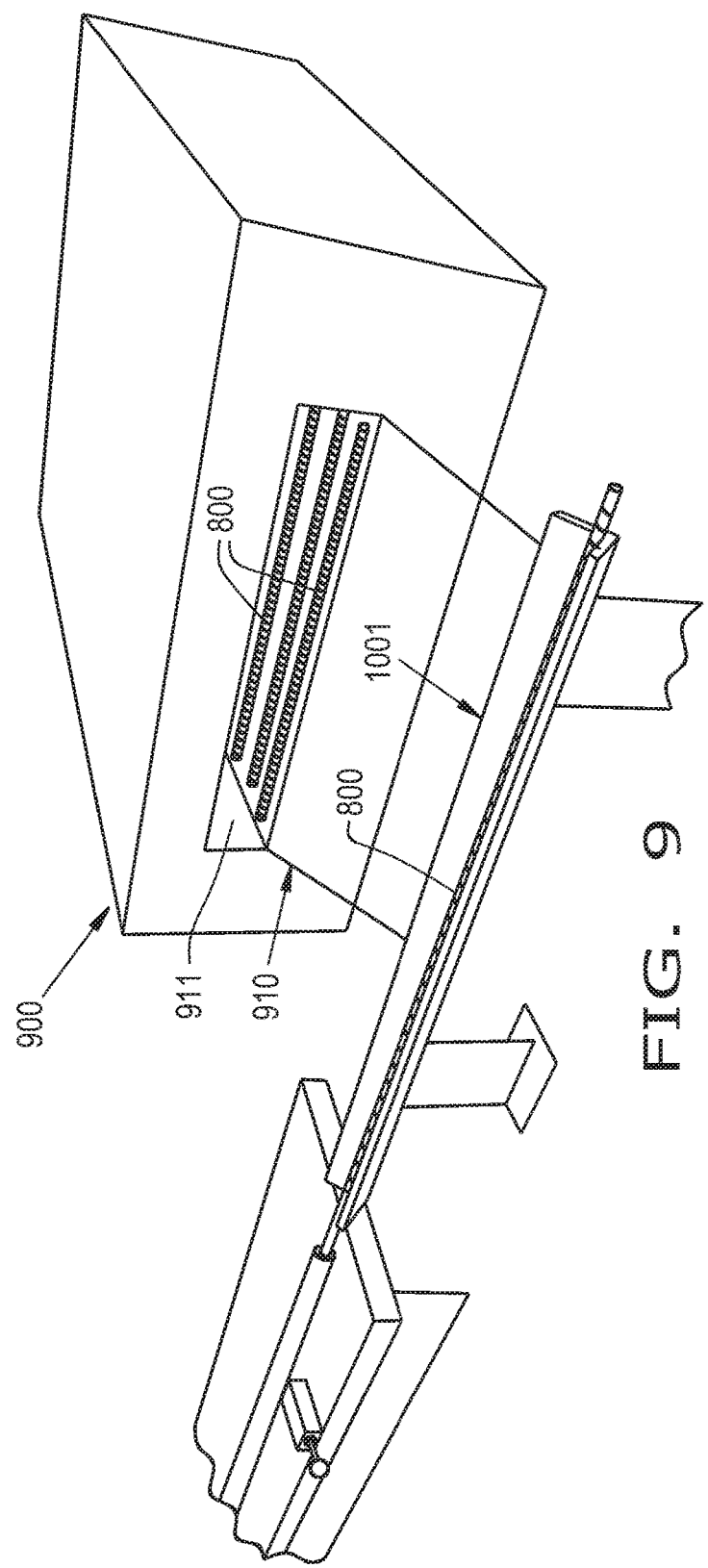
FIG. 9 is a perspective view of an exemplary embodiment of a pre-heating oven for pre-heating the mandrel illustrated in FIG. 8.

Referring specifically now to FIG. 8, an exemplary embodiment of a mandrel 800 that may be used in the method 700 is illustrated. The mandrel 800 includes at least one helical groove 801, which may extend from a first terminal end 802 to a second terminal end 803 that is opposite the first terminal end 802, i.e., the at least one helical groove 801 may extend an entire length of the mandrel 800. In some embodiments, the mandrel 800 includes a plurality of non-overlapping helical grooves 801, such as two non-overlapping helical grooves 801 and 804, to simultaneously form two or more coils, as will be described further herein. The relative dimensions of the helical groove(s) 801, 804, e.g., a width W, a depth D, and a helical angle Hα, may be adjusted to control the shape of the produced coil(s). The mandrel 800 may comprise a metal, such as aluminum, which is relatively lightweight and inexpensive to reduce the power requirements necessary to, for example, rotate the mandrel 800 while producing the coil(s). The dimensions of the mandrel 800, e.g., a length L and a radius R, may be adjusted to control, for example, how many coils may be produced using a single mandrel and the shape of the coils. It should be appreciated that many different configurations of mandrels may be utilized in accordance with the present disclosure to produce coils with different shapes, as will be described further herein.

In some embodiments, the mandrel 800 is pre-heated to a pre-heat temperature in a pre-heat oven 900 (first illustrated in FIG. 9) prior to winding the roving 1401 into the at least one helical groove 801. The pre-heat temperature may be approximately equal to the curing temperature of the uncured material that is coated onto the roving 1401. In some embodiments, the uncured material is a resin material with a curing temperature of approximately 180° F.-250° F. (which is approximately 80° C.-120° C.); in such an instance, the pre-heat temperature of the mandrel 800 may be, for example, between about 160° F. and about 270° C., i.e., within about 20° F. (which is approximately 10° C.) of the curing temperature. Pre-heating the mandrel 800 prior to winding the roving 1401 into the at least one helical groove 801 can reduce the amount of time that the roving 1401 coated with uncured material needs to cure in, for example, the curing oven 1503 to form the composite roving 1601, as will be described further herein. While the mandrel 800 is illustrated as pre-heating in the oven 900, it should be appreciated that the mandrel 800 may be pre-heated in other ways, e.g., by immersion in a hot fluid bath or by flowing electrical current through the mandrel 800. In some embodiments, a plurality of mandrels 800, e.g., two mandrels, three mandrels, five mandrels, ten mandrels, or at least twenty mandrels, may be pre-heated simultaneously in the oven 900 to form coils.

Figure 10:
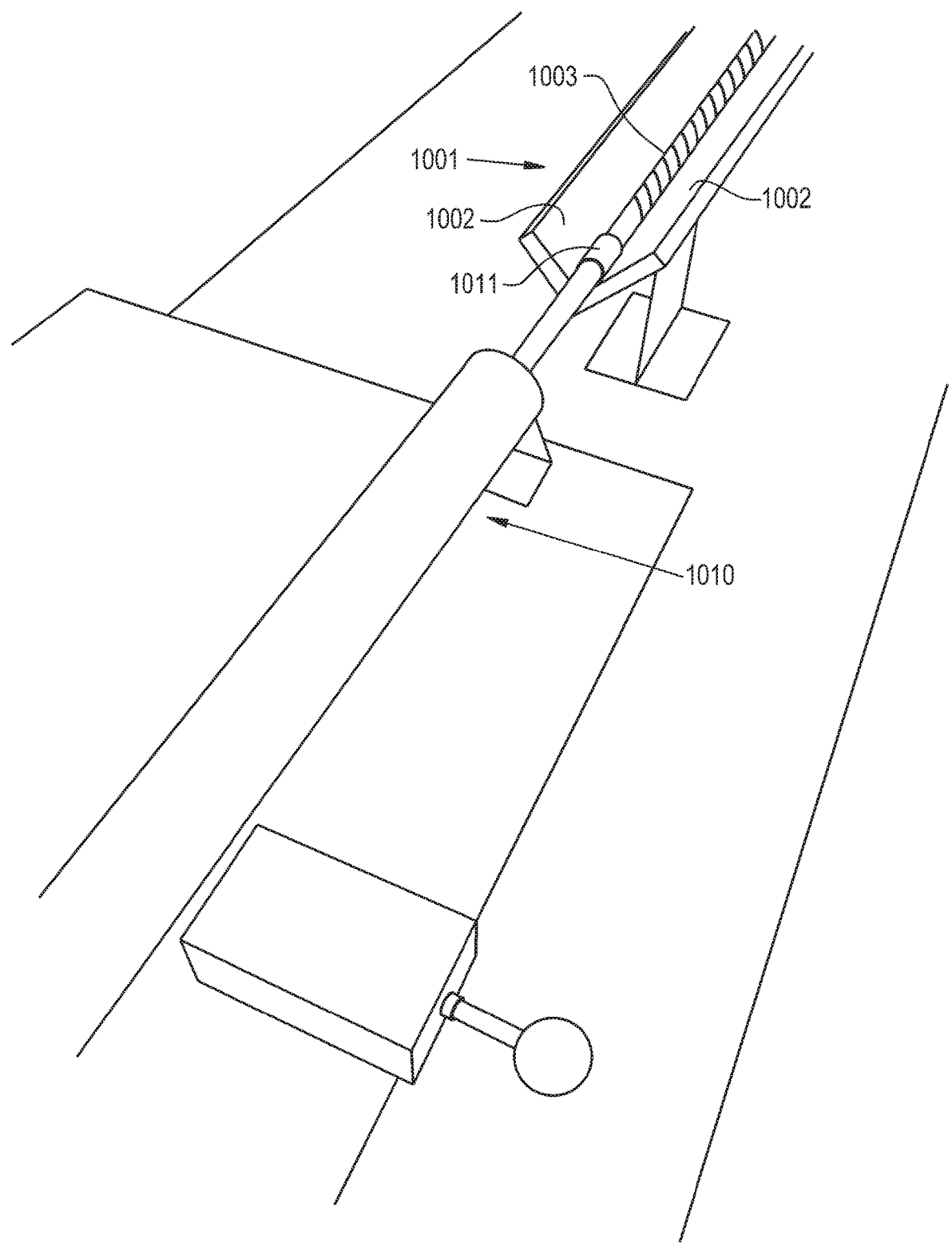
FIG. 10 is a perspective view of an exemplary embodiment of a mandrel pusher for pushing the mandrel illustrated in FIGS. 8-9.
Figure 11:
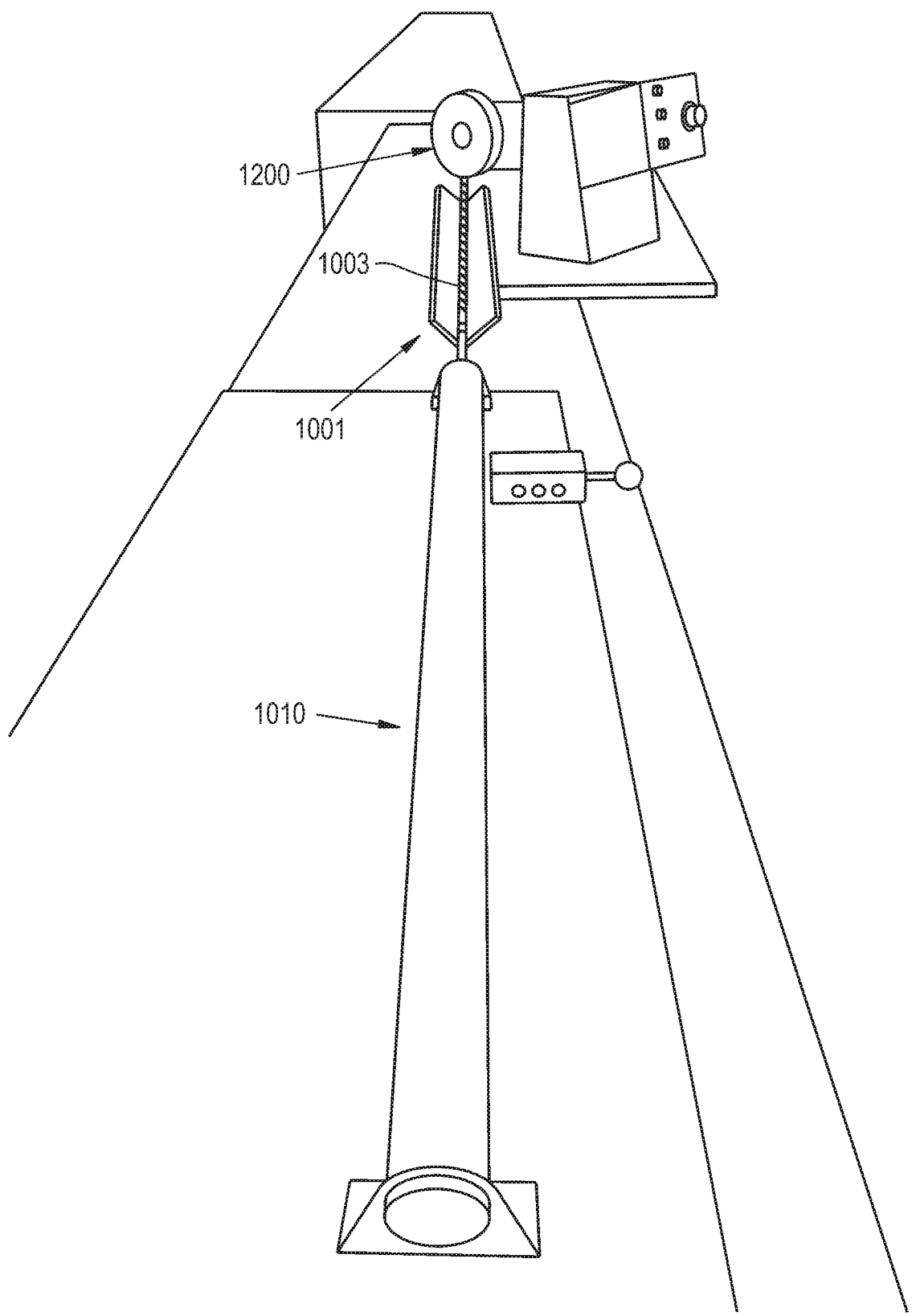
FIG. 11 is another perspective view of the mandrel pusher illustrated in FIG. 10.

In some embodiments, the mandrel 800 leaves the oven 900 after pre-heating and enters a holder 1001, which is illustrated in more detail in FIGS. 10-11. The holder 1001 may be, for example, a V-shaped block with a pair of sidewalls 1002 that meet to form a holding channel 1003, which is sized to hold the mandrel 800 therein. A mandrel pusher 1010, which may be pneumatically powered, may be positioned adjacent to the holder 1001 such that a push rod 1011 of the mandrel pusher 1010 is positioned within the holding channel 1003. When the mandrel 800 enters the holding channel 1003 from the oven 900, the mandrel pusher 1010 may activate and translate the push rod 1011 from an initial position, illustrated in FIG. 10, against the mandrel 800 in the holding channel 1003 to force the mandrel 800 toward a mandrel driver 1200, which is illustrated in greater detail in FIG. 12A. Upon pushing the mandrel 800 into engagement with the mandrel driver 1200, the mandrel pusher 1010 may "reset" and force the push rod 1011 to its initial position in preparation of forcing another mandrel from the oven 900 toward the mandrel driver 1200. In some embodiments, the mandrel pusher 1010 resetting signals for a mandrel feeder 910 adjacent to an oven exit 911 of the oven 900 to dispense another pre-heated mandrel from the oven 900 into the holder 1001, repeating the process of forcing a pre-heated mandrel to the mandrel driver 1200. It should be appreciated the mandrel pusher 1010 may be controlled manually by an operator or automatically by, for example, a processor.

Figure 12A:
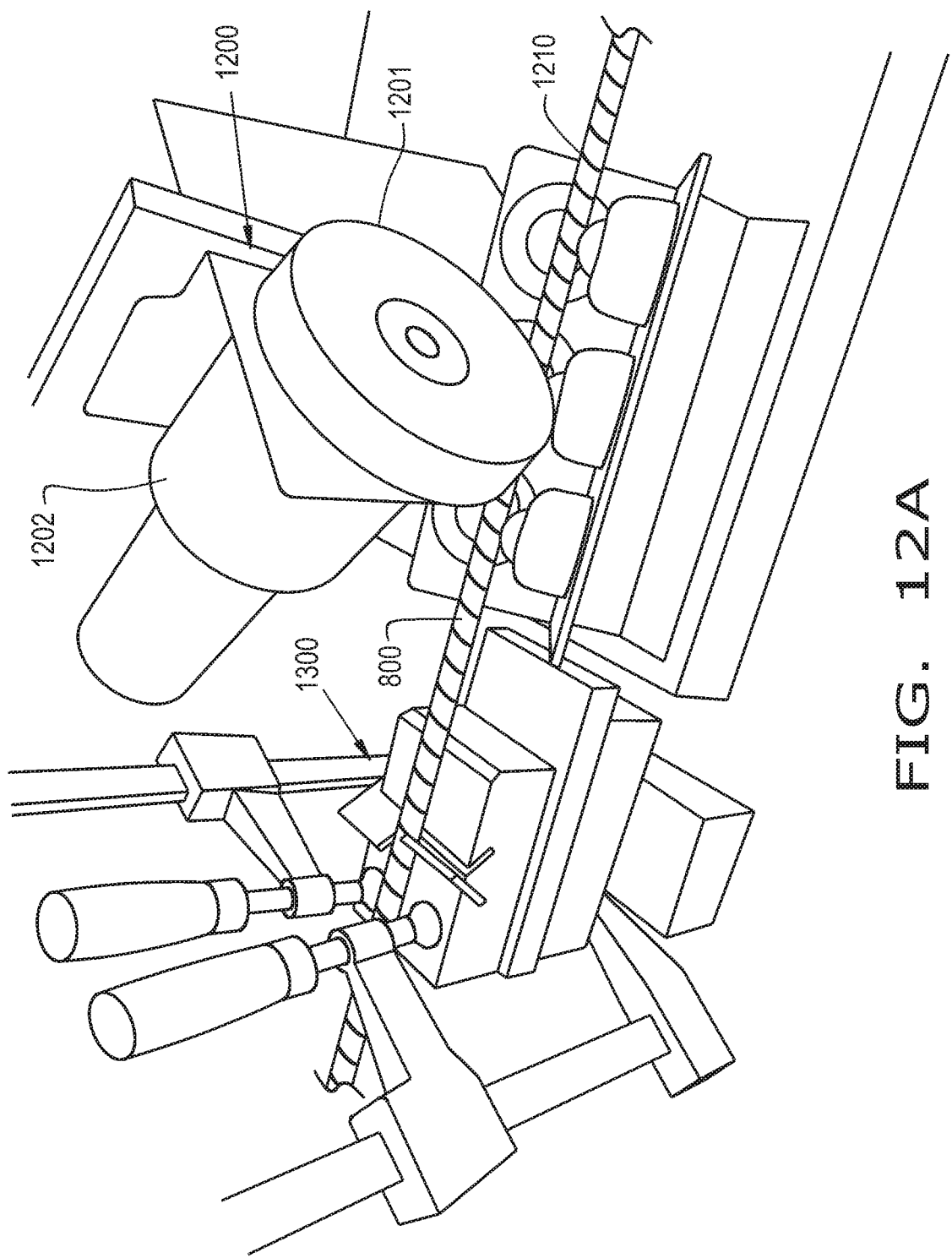
FIG. 12A is a perspective view of an exemplary embodiment of a mandrel driver for rotating the mandrel illustrated in FIG. 8.
Figure 13:
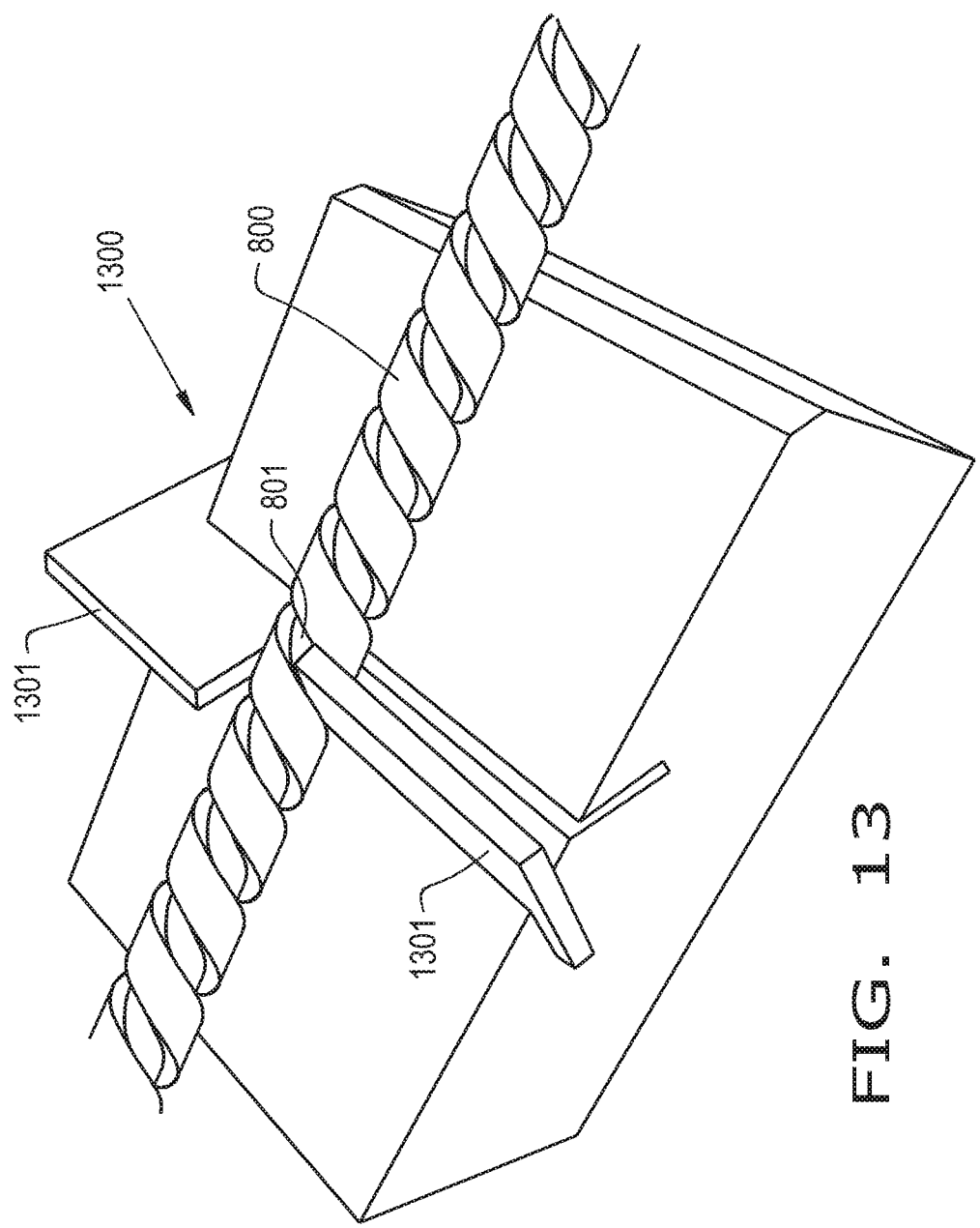
FIG. 13 is a perspective view of an exemplary embodiment of an aligner placed in a helical groove of the mandrel to align the mandrel.

Referring now to FIGS. 12A-13, the mandrel 800 is shown engaged by the mandrel driver 1200, which rotates the mandrel 800. The mandrel driver 1200 may include, for example, a rotatable wheel 1201 that is rotated by an electric rotary motor 1202. As the wheel 1201 engages the mandrel 800 and rotates, rotational energy is transferred from the wheel 1201 to the mandrel 800, causing the mandrel 800 to rotate as well. As the rotatable wheel 1201 rotates the mandrel 800, an additional mandrel 1210 may be pushed by the push rod 1011 against the mandrel 800 to continue linearly translating the mandrel 800 to an aligner 1300, which is illustrated in further detail in FIG. 13. The mandrel 800 and the additional mandrel 1210 may contact one another and couple so that the additional mandrel 1210, when rotated by the wheel 1201, imparts rotational energy to the mandrel 800 to rotate the mandrel 800 even after the mandrel 800 has passed, and is no longer contacting, the wheel 1201.

To couple the mandrel 800 and the additional mandrel 1210 together, and referring now to FIGS. 12B and 12C, one or both of the mandrels, such as the mandrel 800, may be formed with a locking protrusion 805 at the first terminal end 802 and the additional mandrel 1210 may be formed with a corresponding locking groove 1212 at one of its terminal ends 1213. The locking protrusion 805 and the locking groove 1212 may both have a non-circular shape such that, when placed in the locking groove 1212 of the additional mandrel 1210, the locking protrusion 805 engages the locking groove 1212 during rotation. When the locking protrusion 805 engages the locking groove 1212, rotation of the additional mandrel 1210 causes a corresponding rotation of the mandrel 800. In some embodiments, the locking protrusion 805 has a square cross-section and the locking groove 1212 has a complementary shape so the mandrel 800 must only rotate a maximum of 90° before the locking protrusion 805 is properly aligned the locking groove 1212 for coupling. It should be appreciated that the mandrel 800 may also include a locking groove similar to the locking groove 1212 at the second terminal end 803 and the additional mandrel 1210 may include a locking projection similar to the locking protrusion 805 at a terminal end opposite the terminal end 1213.

As illustrated in FIG. 13, the aligner 1300 may include one or more alignment surfaces 1301 that fit within the at least one helical groove 801 of the mandrel 800. The alignment surface(s) 1301 may be placed in the at least one helical groove 801 as the mandrel 800 is pushed by the additional mandrel 1210 and rotated by the wheel 1201. Once the alignment surface(s) 1301 is placed in the at least one helical groove 801 of the mandrel 800, the alignment surface(s) 1301 substantially prevents linear translation of the mandrel 800 except for linear translation that occurs as a result of the helical groove(s) 801 of the mandrel 800 tracking the alignment surface(s) 1301 during rotation of the mandrel 800. In this respect, the aligner 1300 maintains a predictably constant orientation of the mandrel 800 by limiting the linear translation of the mandrel 800.

Figure 14:
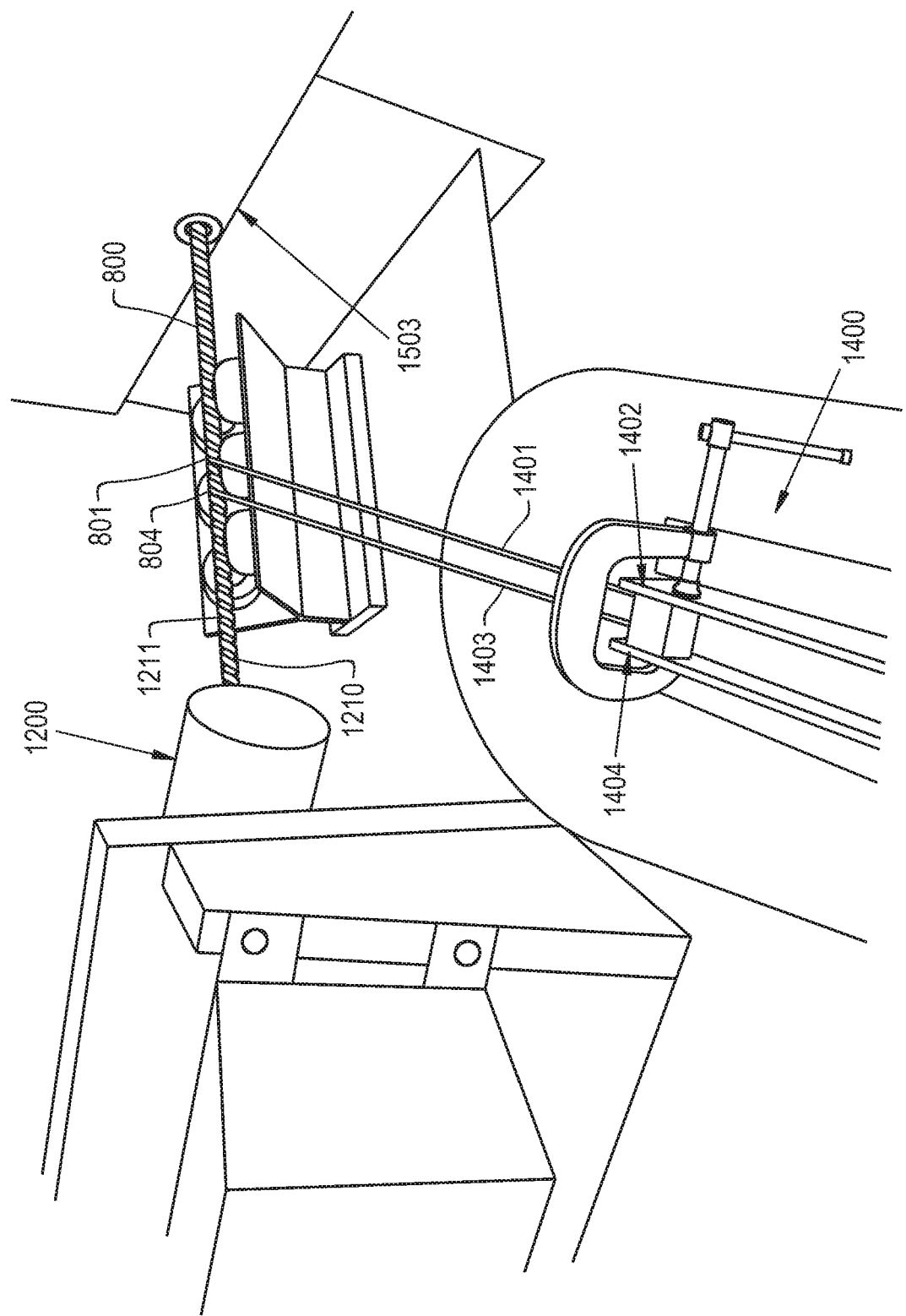
FIG. 14 is a perspective view of an exemplary embodiment of rovings being wound onto the mandrel illustrated in FIG. 8.

Referring now to FIG. 14, an exemplary embodiment of a roving wetout system 1400 for winding the roving 1401 into the helical groove(s) 801 of the mandrel 800 is illustrated. The roving 1401 may be wound into the helical groove(s) 801, for example, from a spool of roving material that is held by the roving wetout system 1400. To wind the roving 1401 into the helical groove(s) 801, the roving 1401 may be initially placed in the helical groove(s) 801. As the mandrel 800 rotates due to, for example, rotation of the wheel 1201, the roving 1401 is wound into the helical groove(s) 801 from the spool. In some embodiments, the roving 1401 comprises a twisted fiberglass material that originates from a spool of twisted fiberglass held by the roving wetout system 1400. It should be appreciated that the roving 1401 may comprise materials other than twisted fiberglass, including but not limited to: poly-paraphenylene terephthalamide, which is supplied by DuPont under the tradename KEVLAR®; carbon fiber; or ultra-high molecular weight polyethylenes (UHMWPE), such as a UHMWPE composition supplied by Honeywell under the tradename SPECTRA®.

To form a composite roving, the roving 1401 is coated with an uncured material, such as a resin material, an epoxy, a polyester, a vinyl ester, a polyurethane, or mixtures thereof. It should be appreciated that the previously described uncured materials are exemplary only and other uncured materials may be used to coat the roving 1401. In some embodiments, the roving 1401 is coated with the uncured material by an applicator 1402 of the roving wetout system 1400 that applies that uncured material to the roving 1401 as the roving 1401 is wound into the helical groove(s) 801. In this respect, the applicator 1402 is placed in the winding path of the roving 1401 into the helical groove(s) 801 so the roving 1401 necessarily passes the applicator 1402, and is thus coated with the uncured material, as the roving 1401 winds into the helical groove(s) 801. In some embodiments, the applicator 1402 is a wheel and the roving 1401 passing through the wheel 1402 rotates the wheel 1402 into a reservoir of uncured material, coating the roving 1401 and resupplying the wheel 1402 with uncured material to coat the roving 1401. While the applicator 1402 is illustrated as physically contacting the roving 1401 to apply uncured material to the roving 1401, in some embodiments the applicator may be, for example, a sprayer that sprays uncured material onto the roving 1401 without physically contacting the roving 1401. It should be appreciated that while the roving 1401 is illustrated as being coated by the uncured material as it is being wound into the helical groove(s) 801, the roving 1401 may alternatively be coated prior to or after winding.

In some embodiments, the roving wetout system 1400 is configured such that two rovings 1401, 1403 simultaneously wind into two non-overlapping helical grooves 801, 804 of the mandrel 800 so two separate coils can be formed on the mandrel 800 simultaneously. When the roving wetout system 1400 is configured for winding two rovings 1401, 1403 into two non-overlapping helical grooves 801, 804 simultaneously, the roving wetout system 1400 may include a second applicator 1404, which may also be a wheel, to coat the other roving 1403 with uncured material as the roving 1403 winds into the helical groove 804. It should be appreciated that the roving wetout system 1400 and mandrel 800 can each be configured to support simultaneously winding more than two rovings into more than two non-overlapping helical grooves by forming, e.g., three or more non-overlapping helical grooves into the mandrel 800 and incorporating three or more spools of roving material in the roving wetout system 1400 to wind into the three or more non-overlapping helical grooves as the mandrel 800 rotates.

In some embodiments, the roving(s) 1401, 1403 wound into the helical groove(s) 801, 804 of the mandrel 800 is also wound into one or more helical grooves 1211 of the additional mandrel 1210 that is coupled to the mandrel 800. In this sense, the roving(s) 1401, 1403 continuously winds into a series of helical grooves 801, 804, 1211 of multiple mandrels 800, 1210, linking the mandrels 800, 1210 together with the roving(s) 1401, 1403. By continuously winding the roving(s) 1401, 1403 from the roving wetout system 1400 into the helical grooves 801, 804 1211 of multiple mandrels 800, 1210 that are in series, production of coils can continue with minimal interruptions to, for example, place the roving(s) 1401, 1403 in the helical groove(s) 801, 804, 1211 of the mandrels 800, 1210 after the helical groove(s) 801, 804, 1211 of each mandrel 800, 1210 has been filled with the roving(s) 1401, 1403. While the roving(s) 1401, 1403 is illustrated as linking together two mandrels 800, 1210, it should be appreciated that one or more continuous rovings 1401, 1403 may link more than two mandrels together, e.g., three mandrels, five mandrels, or more than five mandrels.

Figure 15:
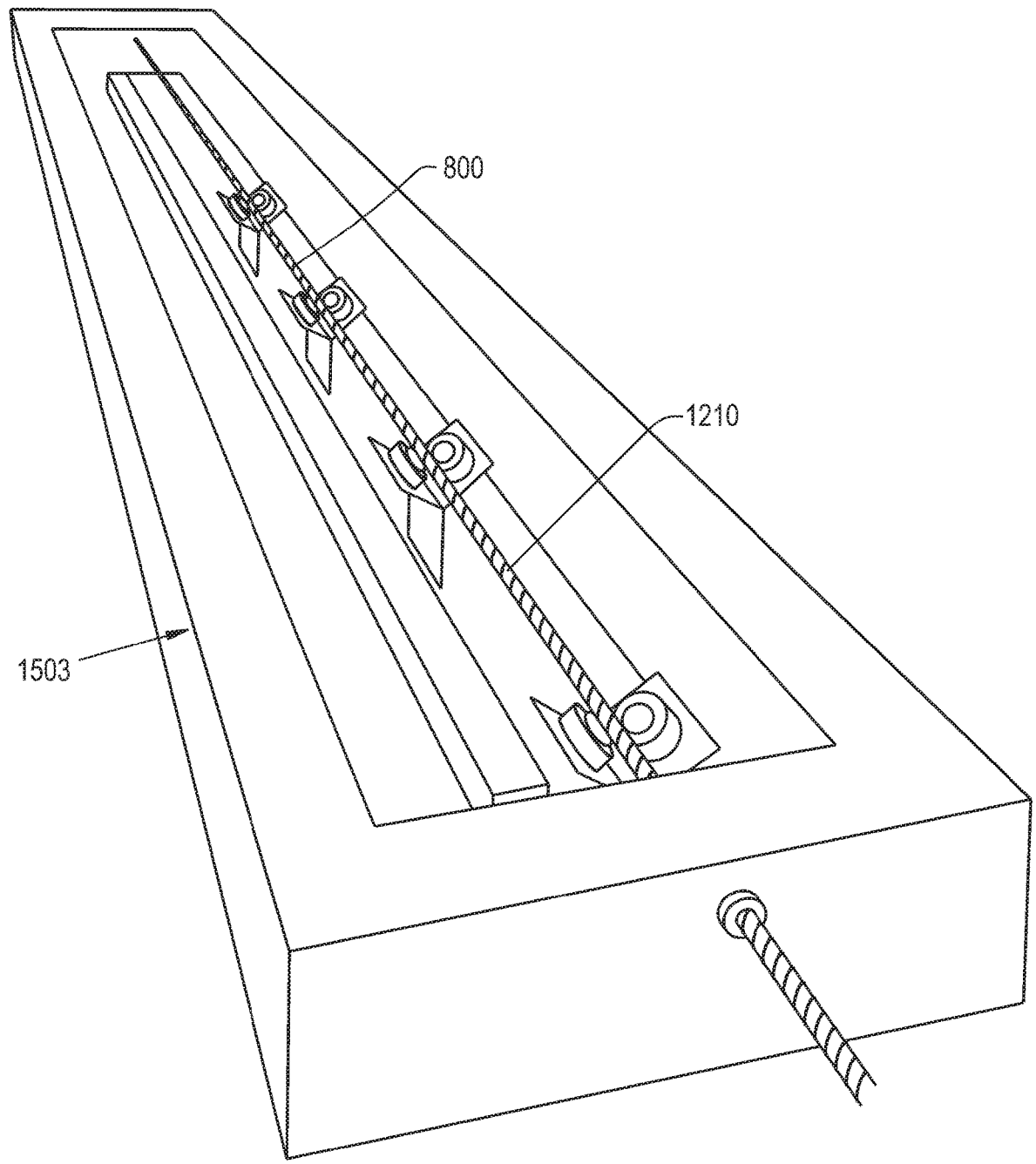
FIG. 15 is a perspective view of the mandrel and wound rovings illustrated in FIG. 14 placed in an oven for heating.

With continued reference to FIG. 14, and referring now to FIG. 15 as well, the mandrel 800 with the coated rovings 1401, 1403 wound into the one or more helical grooves 801, 804 is heated by, for example, placing the mandrel 800 into the curing oven 1503, which is set to heat the coated rovings 1401, 1403 to the curing temperature of the uncured material. The mandrel 800 and coated rovings 1401, 1403 are left in the curing oven 1503 for a time period that is sufficient to allow the uncured material to cure, forming composite rovings 1601 that comprise the original roving material and cured material that was applied to the rovings 1401, 1403. In some embodiments, the curing temperature is around 180° F.-250° F., but it should be appreciated that the curing temperature depends on the uncured material coating the roving(s) 1401, 1403. The time period that the coated roving(s) 1401, 1403 is heated to form the composite roving depends on the uncured material coating the roving(s) 1401, 1403, but should generally be as short as feasible to increase the production rate of coils. In some embodiments, the time period that the coated roving(s) 1401, 1403 spends heating to cure the uncured material is between about 10 minutes to 30 minutes. In some embodiments, the mandrel 800 is pre-heated to a pre-heat temperature that is close to the curing temperature to reduce the amount of time needed for the coated roving(s) 1401, 1403 to reach the curing temperature and cure the uncured material. Thus, pre-heating the mandrel 800 can reduce the time needed to form the composite rovings 1601 and increase the rate at which composite rovings 1601 are produced. In some embodiments, the additional mandrel 1210 linked to the mandrel 800 can force the mandrel 800 through the curing oven 1503 by, for example, pushing the mandrel 800 through the curing oven 1503. The additional mandrel 1210 may be pushed by, for example, yet another mandrel that is being linearly translated by the mandrel driver 1200. Such an arrangement allows multiple mandrels to be used simultaneously for coil production in a simple and efficient manner.

Figure 16:
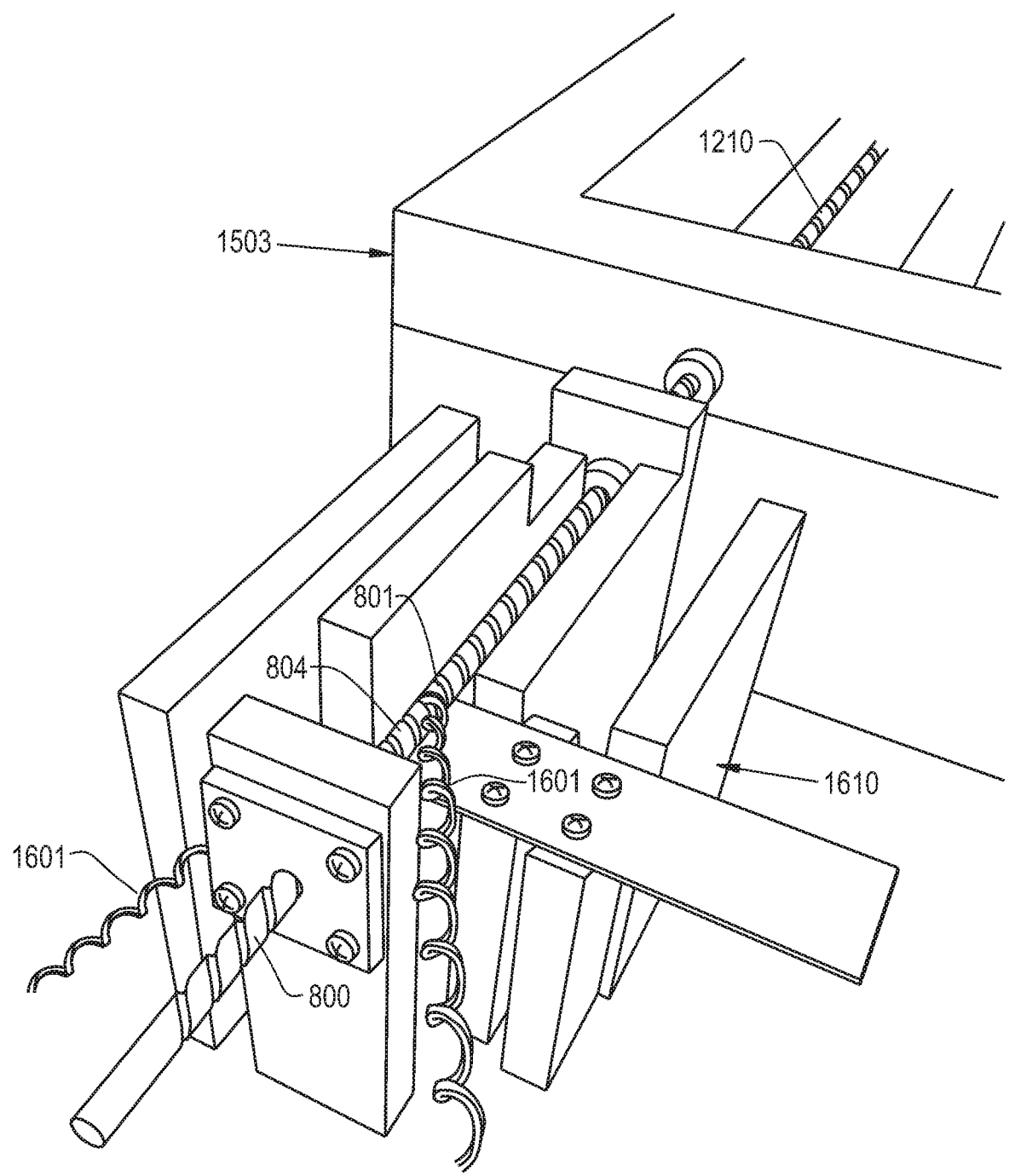
FIG. 16 is a perspective view of composite rovings being stripped from the mandrel illustrated in FIGS. 14-15.
Figure 17:
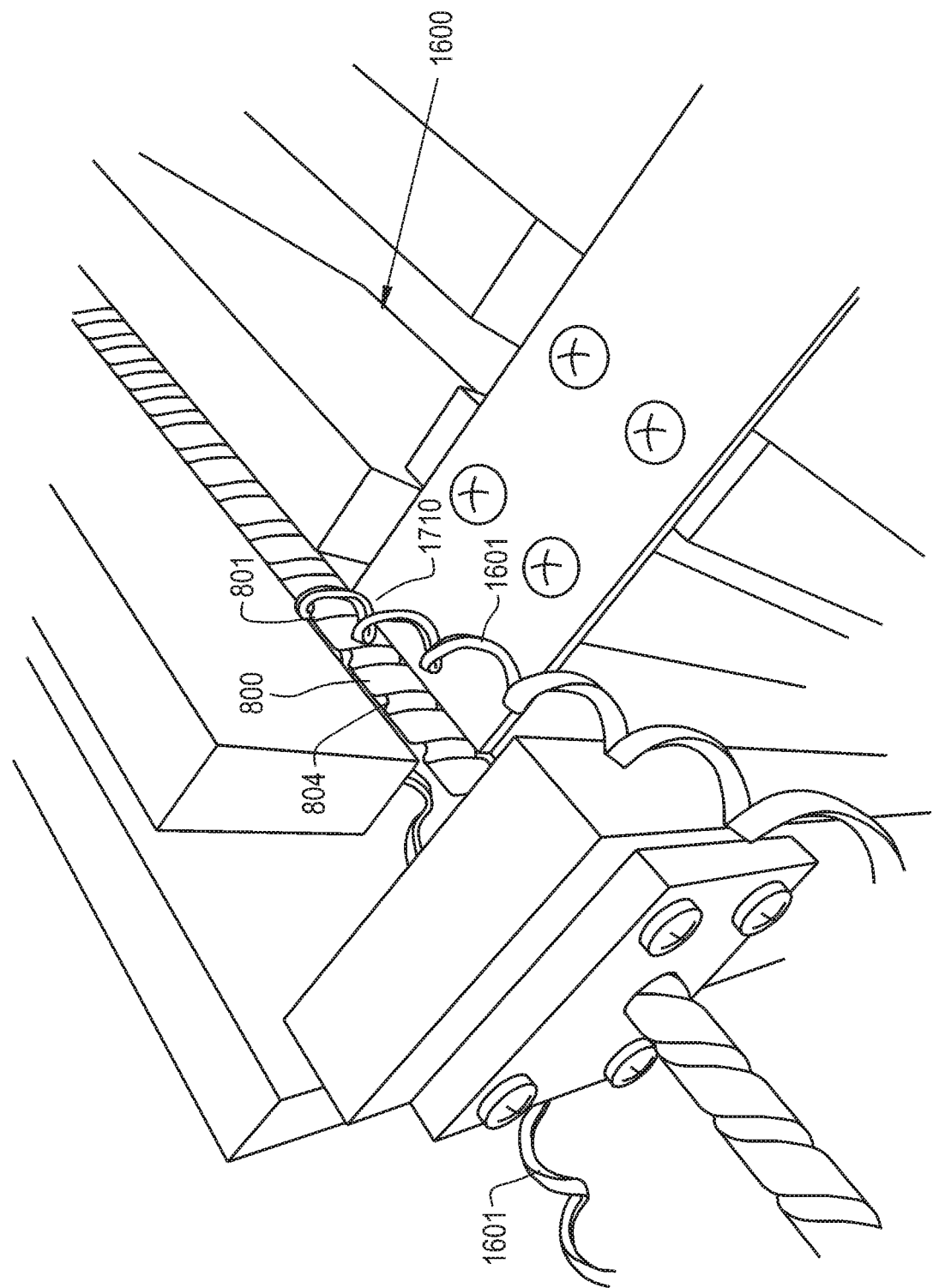
FIG. 17 is a close-up view of the composite rovings illustrated in FIG. 16 being stripped from the mandrel.

Referring now to FIGS. 16 and 17, the mandrel 800 is illustrated coming out of the curing oven 1503 with composite rovings 1601 formed in the helical grooves 801, 804. Once formed, the composite rovings 1601 are ready to be stripped from the mandrel 800 and used to form, for example, a driveshaft. To strip the composite rovings 1601 from the mandrel 800, the mandrel 800 may pass through a stripping assembly 1610 that includes one or more stripping surfaces 1710 (illustrated in greater detail in FIG. 17) placed next to the helical grooves 801, 804 of the mandrel 800. Because the mandrel 800 has two helical grooves 801, 804 with composite rovings 1601, the stripping assembly 1610 includes two stripping surfaces 1710, with each stripping surface 1710 placed next to a respective helical groove 801, 804. As the mandrel 800 rotates, the composite rovings 1601 are forced against the stripping surfaces 1710, stripping the composite rovings 1601 from the mandrel 800, as illustrated. In this sense, the stripping assembly 1610 can continuously strip composite rovings 1601 from the mandrel 800, and subsequent mandrels. While the stripping surfaces 1710 are illustrated and described as being placed next to the helical grooves 801, 804 to strip composite rovings 1601 from the mandrel 800, the stripping surfaces 1710 may also be placed in a respective helical groove 801, 804 to similarly strip composite rovings 1601 from the mandrel 800. As can be appreciated from FIGS. 16 and 17, the composite rovings 1601 that are stripped from the mandrel 800 maintain a helical shape after being stripped from the mandrel 800, i.e., the stripped composite rovings 1601 are coils with a shape depending on the shape of the helical groove 801, 804 in which the composite roving 1601 is formed. Once stripped from the mandrel 800, the coils can then be cut to size and/or further processed to form a flexible driveshaft, as will be described further herein.

Figure 18:
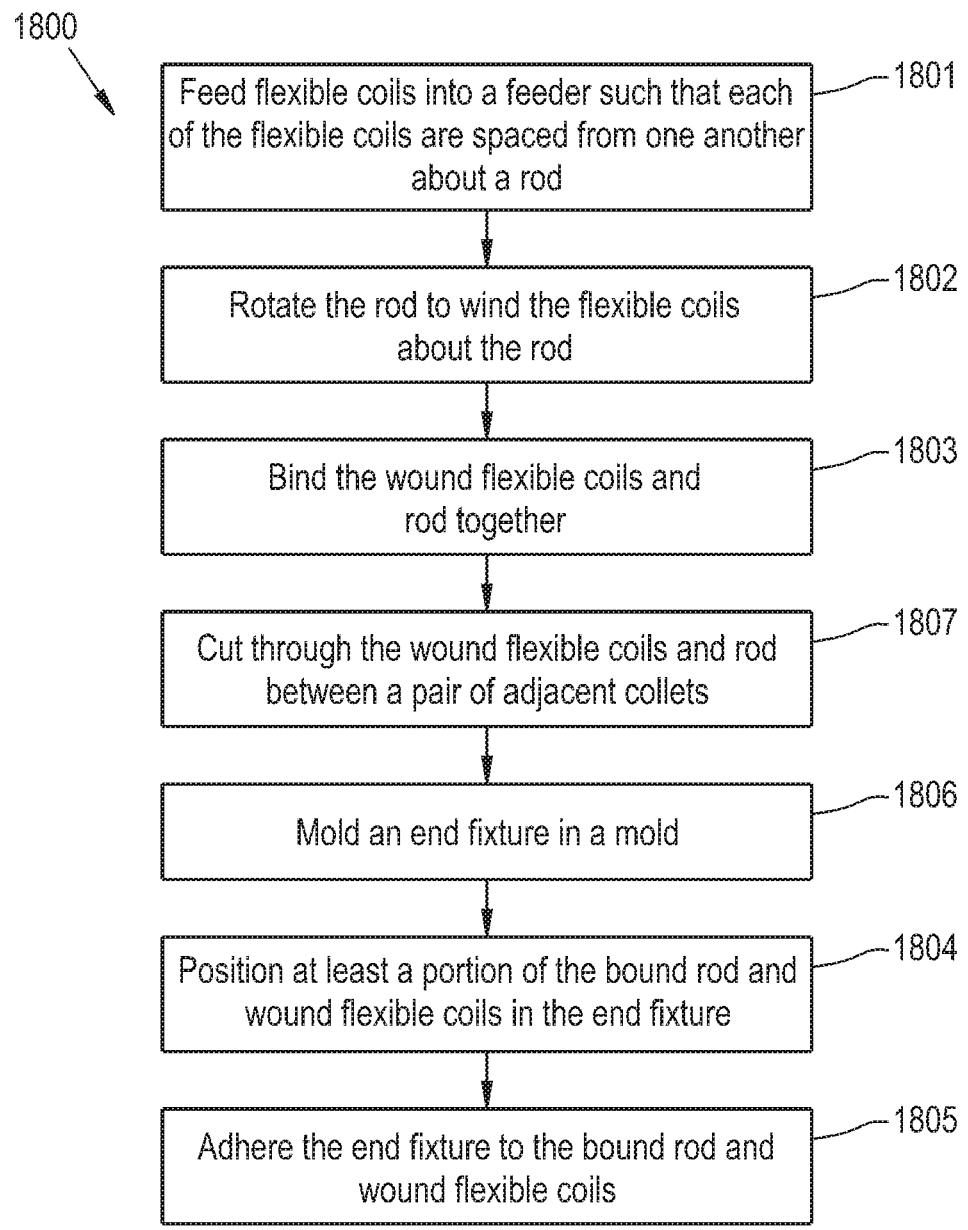
FIG. 18 is a flow chart illustrating an exemplary embodiment of a method of forming a flexible driveshaft for a surgical instrument.

Referring now to FIGS. 18-26, an exemplary embodiment of a method 1800 of forming a flexible driveshaft, such as flexible driveshaft 10 or 40, for a surgical instrument is illustrated. Referring specifically to FIG. 18, the method 1800 is illustrated in flowchart form and includes feeding 1801 a plurality of flexible coils, such as the stripped composite rovings 1601, into a feeder 1910 (illustrated in FIG. 19) such that each of the plurality of flexible coils 1601 are spaced from one another about a rod 1920 (first illustrated in FIG. 19). The rod 1920 is rotated 1802 to wind the flexible coils 1601 about the rod 1920. When the flexible coils 1601 are wound about the rod 1920, the wound flexible coils 1601 and the rod 1920 are bound 1803 together. In some embodiments, the method 1800 further includes positioning 1804 at least a portion of the bound rod 1920 and wound flexible coils 1601 in an end fixture 2410, 2510 (first illustrated in FIGS. 24-25) and adhering 1805 the end fixture 2410, 2510 to the bound rod 1920 and wound flexible coils 1601. In some embodiments, the method 1800 further includes molding 1806 the end fixture 2410 in a mold 2301 (illustrated in FIG. 23), with the end fixture 2410 being adhered 1805 to the bound rod 1920 and wound flexible coils 1601 in the mold 2301. In some embodiments, the binding 1803 includes binding one or more collets 2010, 2210A, 2210B, 2210C (first illustrated in FIGS. 20 and 22) to the wound flexible coils 1601 and rod 1920. When multiple collets 2210A, 2210B, 2210C are bound to the wound flexible coils 1601 and the rod 1920, the method 1800 may further include cutting 1807 through the wound flexible coils 1601 and the rod 1920 in between a pair of adjacent collets 2210A, 2210B, 2210C. The method 1800 is described in further detail herein with reference to FIGS. 19-26

Figure 19:
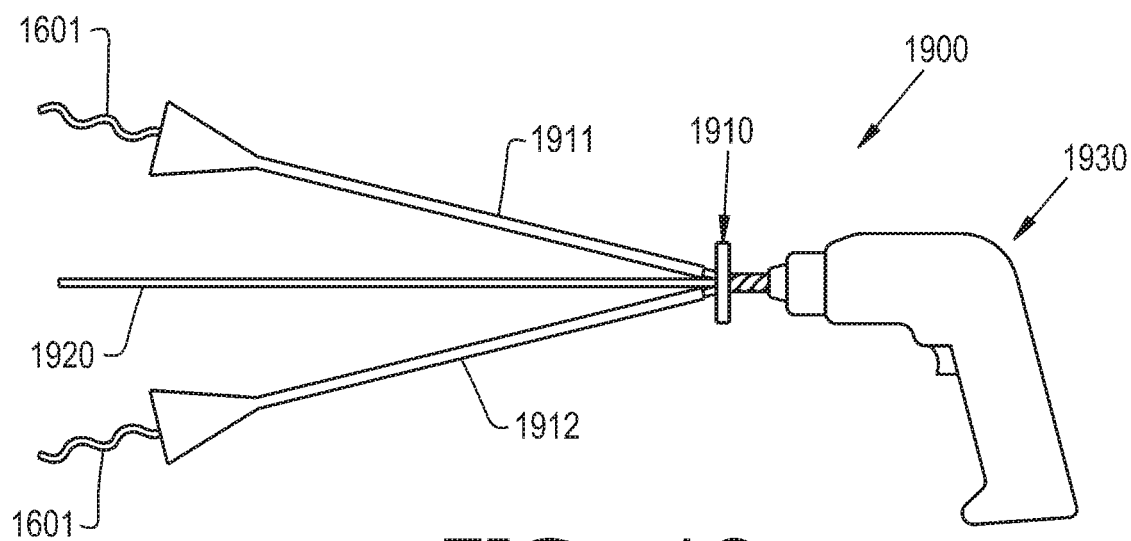
FIG. 19 is a side view of an exemplary embodiment of a winding station for winding flexible coils onto a rod.

Referring now to FIG. 19, an exemplary embodiment of a winding station 1900 for winding the flexible coils 1601 about a rod 1920 is illustrated. The winding station 1900 includes a feeder 1910 through which the rod 1920 passes and which may be rotationally static relative to the rod 1920. In some embodiments, the winding station 1900 includes one or more feed tubes 1911, 1912 surrounding and guiding the flexible coils 1601 that are being fed to the feeder 1910. The flexible coils 1601 may be initially wound around the rod 1920 by, for example, an operator prior to rotating the rod 1920. When the flexible coils 1601 are fed to the feeder 1910, rotation of the rod 1920 acts to wind the flexible coils 1601 about the rod 1920 and pull additional lengths of the flexible coils 1601 to the feeder 1910, allowing for feeding and winding of an entire length of the flexible coils 1601 about the rod 1920 so long as the rod 1920 rotates. As the flexible coils 1601 wind about the rod 1920, the feeder 1910 can ensure that the flexible coils 1601 wind about the rod 1920 in a properly oriented manner and prevent, e.g., the flexible coils 1601 from snaring one another during rotation of the rod 1920. It should be appreciated that while the rod 1920 is shown being rotated by an electrically powered rotary drill 1930, the rod 1920 may be rotated in any suitable manner to wind the flexible coils 1601 about the rod 1920. In some embodiments, the rod 1920 comprises a flexible material to form a fully flexible driveshaft. As used herein, a "flexible" material is one that allows approximately 90 degrees or more of deformation from an unflexed state without fracturing. Exemplary flexible materials that may be used include, but are not limited to: nylon; polyoxymethylenes, such as DELRIN® supplied by DuPont; and various types of thermoplastics. In some embodiments, the rod 1920 comprises a relatively rigid material, such as stainless steel.

Figure 20:
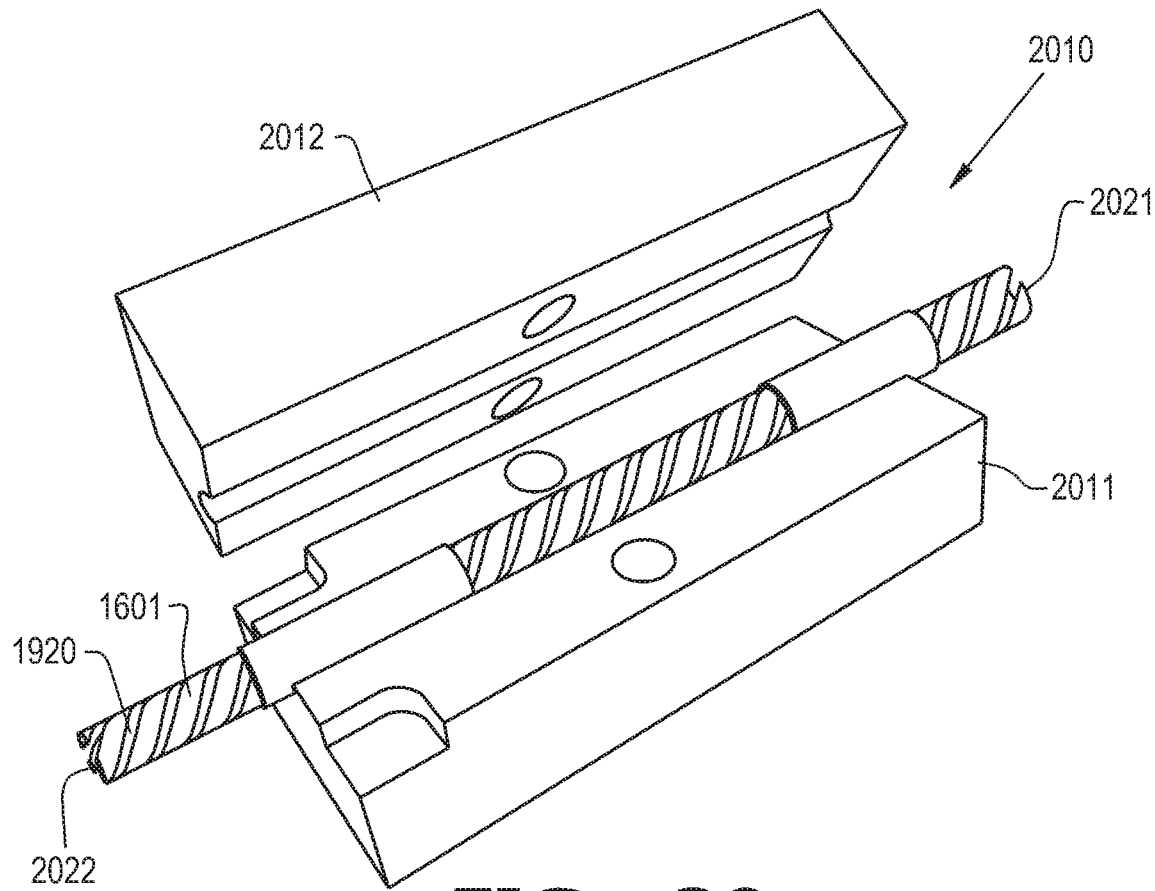
FIG. 20 is a perspective view of an exemplary embodiment of an open collet for binding the wound flexible coils and rod illustrated in FIG. 19 together.
Figure 21:
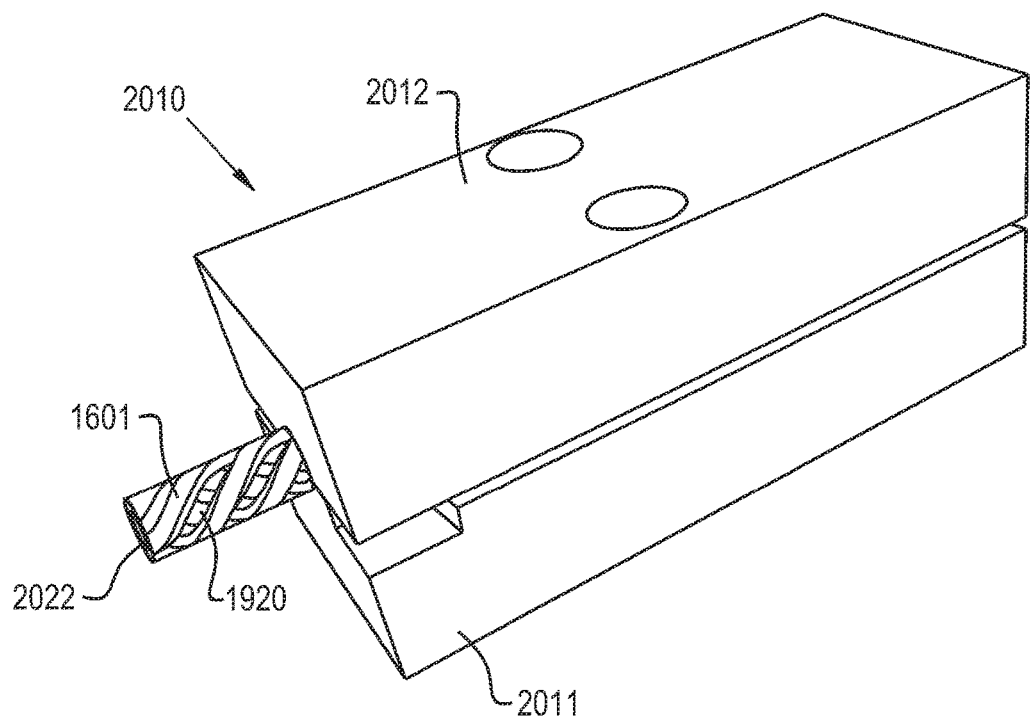
FIG. 21 is a perspective view of the collet illustrated in FIG. 20 when the collet is closed, binding the wound flexible coils and rod together.

When the flexible coils 1601 are wound about the rod 1920, and referring now to FIGS. 20-21, the wound flexible coils 1601 and the rod 1920 are bound together using, for example, a collet 2010. In some embodiments, the collet 2010 is a split collet having a first portion 2011 and a second portion 2012 that separate from one another, as illustrated in FIG. 20, to allow placement of the wound flexible coils 1601 and the rod 1920 between the two portions 2011, 2012 before rejoining the portions 2011, 2012 together to bind the wound flexible coils 1601 and the rod 1920 together, as illustrated in FIG. 21. In some embodiments, the two portions 2011, 2012 of the collet 2010 are held together by, for example, a clamp, such as a spring clamp. When the collet 2010 is closed and binding the wound flexible coils 1601 and the rod 1920 together, the wound flexible coils 1601 are, generally, less prone to shifting their position relative to the rod 1920, making the bound flexible coils 1601 and rod 1920 easier to handle. In some embodiments, one or both terminal ends 2021, 2022 of the wound flexible coils 1601 and the rod 1920 extend out of the collet 2010 when the collet 2010 binds the flexible coils 1601 and rod 1920 together, the significance of which will be described further herein. It should be appreciated that various lengths of the flexible coils 1601 and rod 1920 may be exposed when the collet 2010 is closed to bind the wound flexible coils 1601 and the rod 1920 together.

Figure 22:
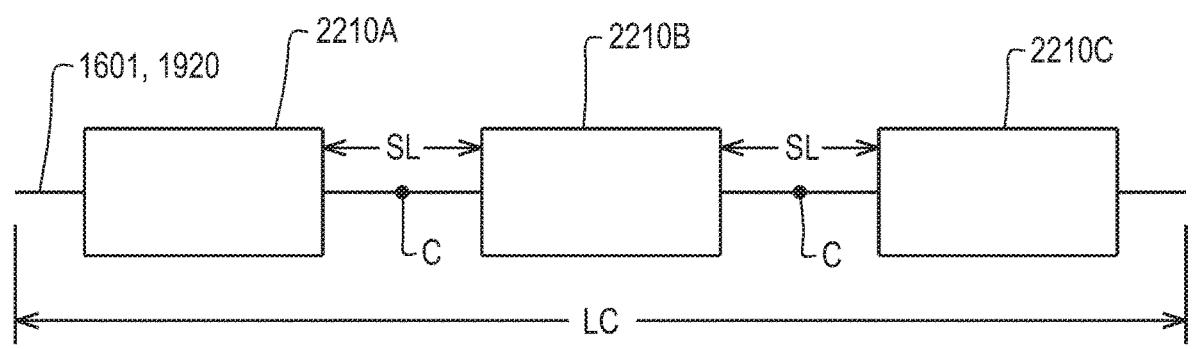
FIG. 22 is a schematic view of an exemplary embodiment for forming multiple lengths of bound flexible coils and rod from a single length of flexible coils wound about a rod.

Referring now to FIG. 22, an exemplary way of forming multiple bound lengths of wound flexible coils 1601 with the rod 1920 is illustrated. A length LC of flexible coils 1601 wound about the rod 1920 is provided and multiple collets 2210A, 2210B, 2210C are attached to the wound flexible coils 1601 and rod 1920 to bind the wound flexible coils 1601 and rod 1920 together. In some embodiments, the collets 2210A, 2210B, 2210C are evenly spaced from one another to form equivalent sub-lengths SL of the wound flexible coils 1601 and rod 1920 between adjacent collets, such as between collet 2210A and 2210B. When the collets 2210A, 2210B, 2210C are attached to and bind the wound flexible coils 1601 and rod 1920 together, the length LC may be cut by, for example, cutting through the wound flexible coils 1601 and rod 1920 at a center C of each sub-length SL between two adjacent collets 2210A, 2210B, 2210C. After cutting through the wound flexible coils 1601 and rod 1920 between the collets 2210A, 2210B, 2210C, three bound lengths of wound flexible coils 1601 and rod 1920 are formed, with each bound length having a respective collet 2210A, 2210B, 2210C binding the wound flexible coils 1601 and rod 1920 together.

Figure 23:
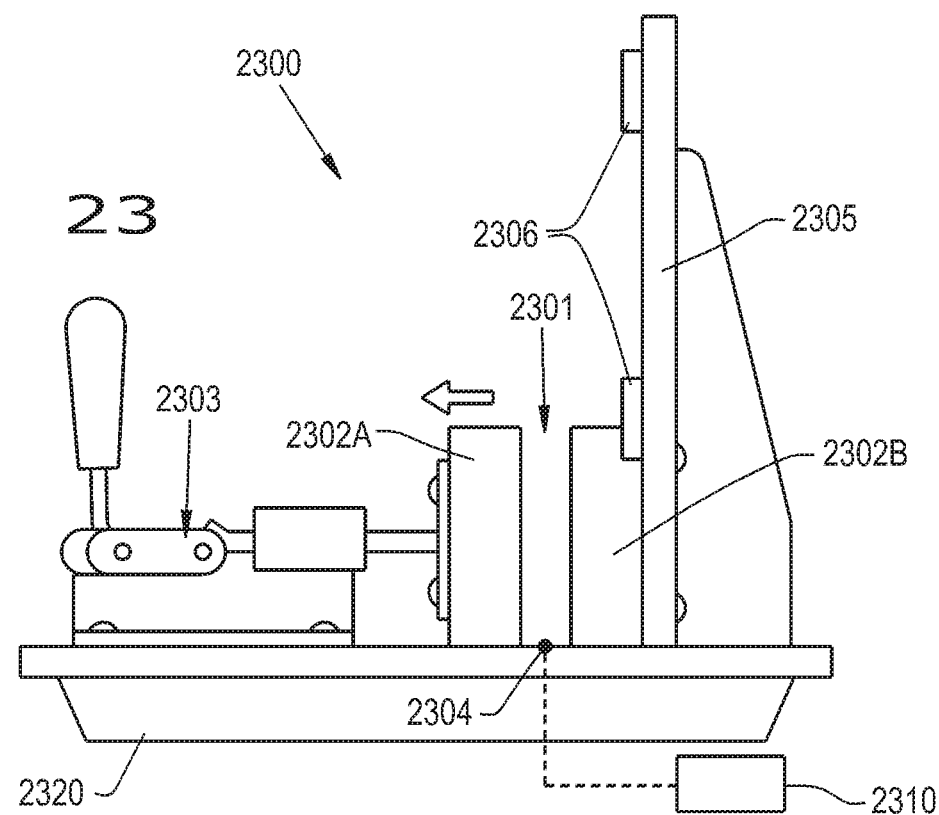
FIG. 23 is a side view of an exemplary embodiment of a finishing assembly with an open mold.

Referring now to FIGS. 23-26, an exemplary way of forming a driveshaft, such as driveshaft 10 illustrated in FIG. 1 with couplers 12, 14, a power drive attachment 18, and a surgical cutter 20, is illustrated. Referring specifically now to FIG. 23, a finishing assembly 2300 may be placed on a carousel 2320 and include a mold 2301 with mold parts 2302A, 2302B that can be opened and closed by, for example, a lever assembly 2303 connected to the mold part 2302A. In some embodiments, the mold 2301 fluidly communicates with a material reservoir 2310, which holds molding material such as a polymer, via a through-hole 2304 that extends into the mold 2301. The mold 2301 may be placed adjacent to a support surface 2305 with alignment protrusions 2306 to properly position and orient a driveshaft that is being formed, as will be described further herein. While only one finishing assembly 2300 is illustrated on the carousel 2320 in FIGS. 23-26, it should be appreciated that multiple similar finishing assemblies 2300 may be placed on the carousel 2320 to simultaneously form driveshafts. In some embodiments, the number of finishing assemblies 2300 on the carousel 2320 may be two, five, or more than ten, depending on the desired output of driveshafts.

Figure 24:
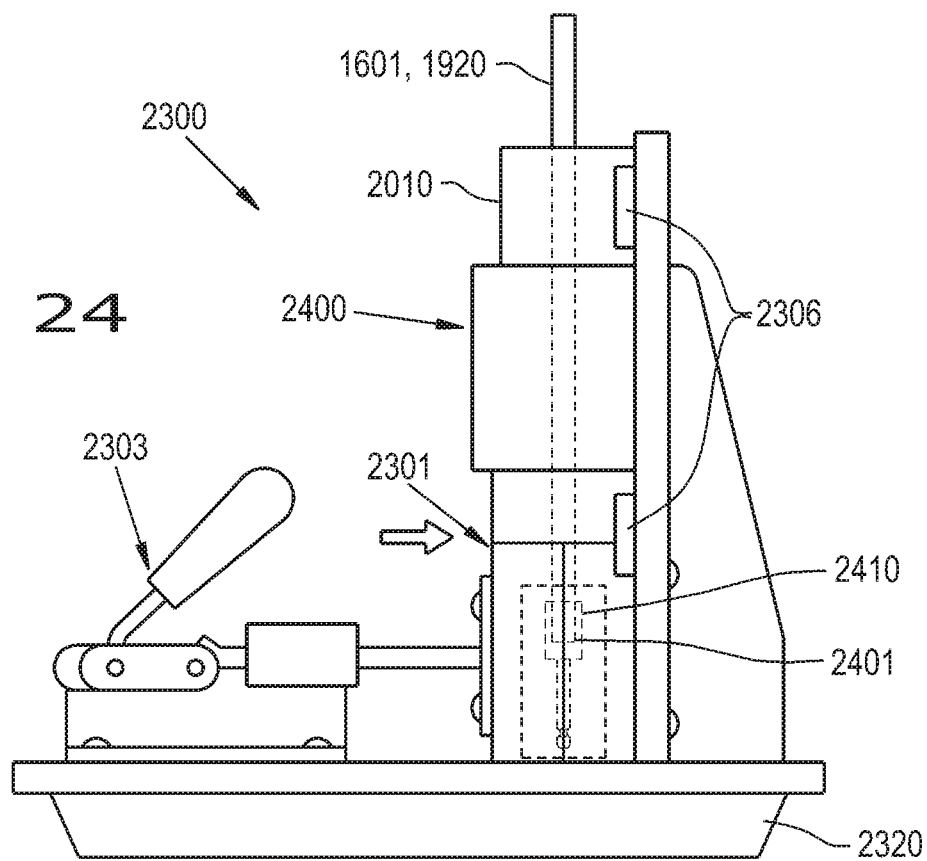
FIG. 24 is a side view of the finishing assembly illustrated in FIG. 23 with a bound assembly and an end fixture placed in the mold, which has been closed.

Referring specifically now to FIG. 24, a bound assembly 2400 including the collet 2010 binding the wound flexible coils 1601 and rod 1920 together is illustrated with a first portion 2401 of the flexible coils 1601 and rod 1920, which extend out of the collet 2010, placed in the mold 2301. An end fixture 2410, which may include coupler 12 and power drive attachment 18, is placed in the mold 2301 prior to the first portion 2401 of the flexible coils 1601 and rod 1920. A measured amount of adhesive, such as cyanoacrylate, is dispensed into the mold with the end fixture 2410 and the first portion 2401 of the flexible coils 1601 and rod 1920 is positioned in the end fixture 2410 while the mold 2301 is open. The collet 2010 is placed between the alignment protrusions 2306 to ensure that the collet 2010, and thus the flexible coils 1601 and rod 1920, is properly positioned with respect to the end fixture 2410. The mold 2301 is then closed to allow the adhesive to cure, adhering the end fixture 2410 to the bound rod 1920 and wound flexible coils 1601. The closed mold 2301 may be transported by the carousel 2320 to a curing station including an oven to heat the adhesive in the mold 2301 and firmly adhere the end fixture 2410 to the first portion 2401 of the flexible coils 1601 and rod 1920. In some embodiments, the carousel 2320 transports the closed mold 2301 through the curing station oven, with the speed of the carousel 2320 being chosen to allow the adhesive to cure in the closed mold 2301 during travel through the curing station oven.

In some embodiments, the end fixture 2410 is molded in the mold 2301 prior to placing the first portion 2401 of the flexible coils 1601 and rod 1920 in the mold 2301. To mold the end fixture 2410, a measured amount of adhesive material may be dispensed into the mold 2301 from the material reservoir 2310 via the through-hole 2304 when the mold 2301 is closed. In some embodiments, the mold 2301 is cleaned and coated with a release agent prior to dispensing the adhesive material into the mold 2301 to prevent the molding material from sticking to the mold 2301 after the molding material has cooled and hardened. Once the molding material has cooled and hardened to form the end fixture 2410, the molded end fixture 2410 may be removed from the mold 2301 for inspection and cleaning before being replaced in the mold 2301 for adhering with the first portion 2401 of the flexible coils 1601 and rod 1920.

Figure 25:
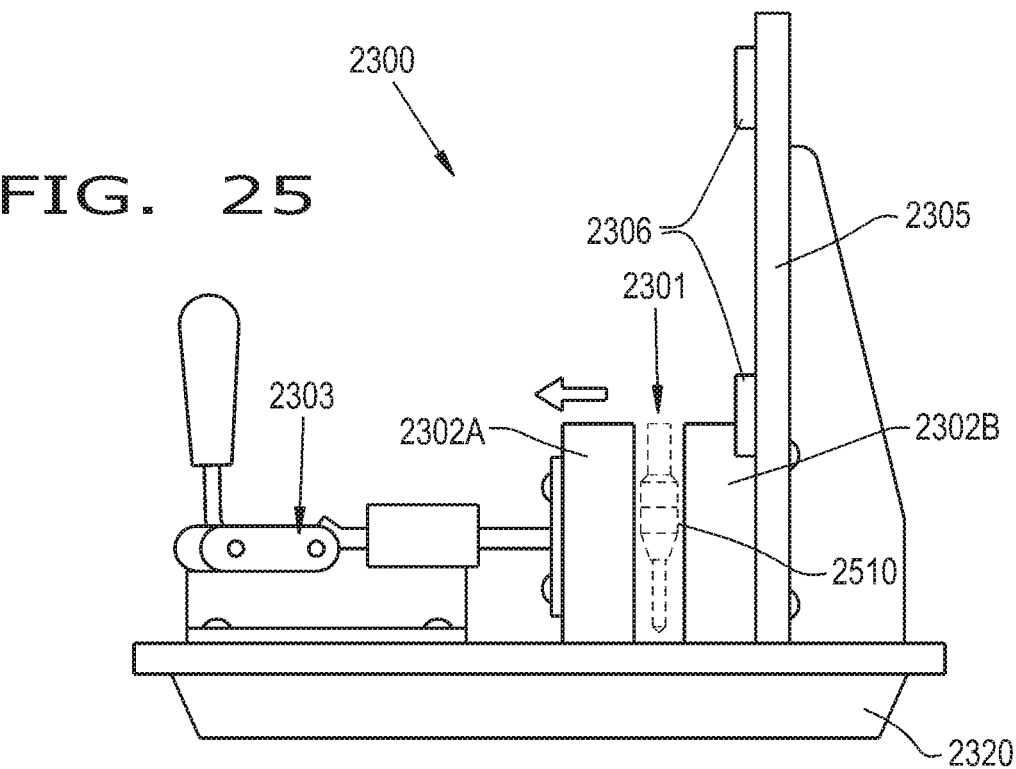
FIG. 25 is a side view of the finishing assembly illustrated in FIGS. 23-24 with another end fixture placed in the open mold.
Figure 26:
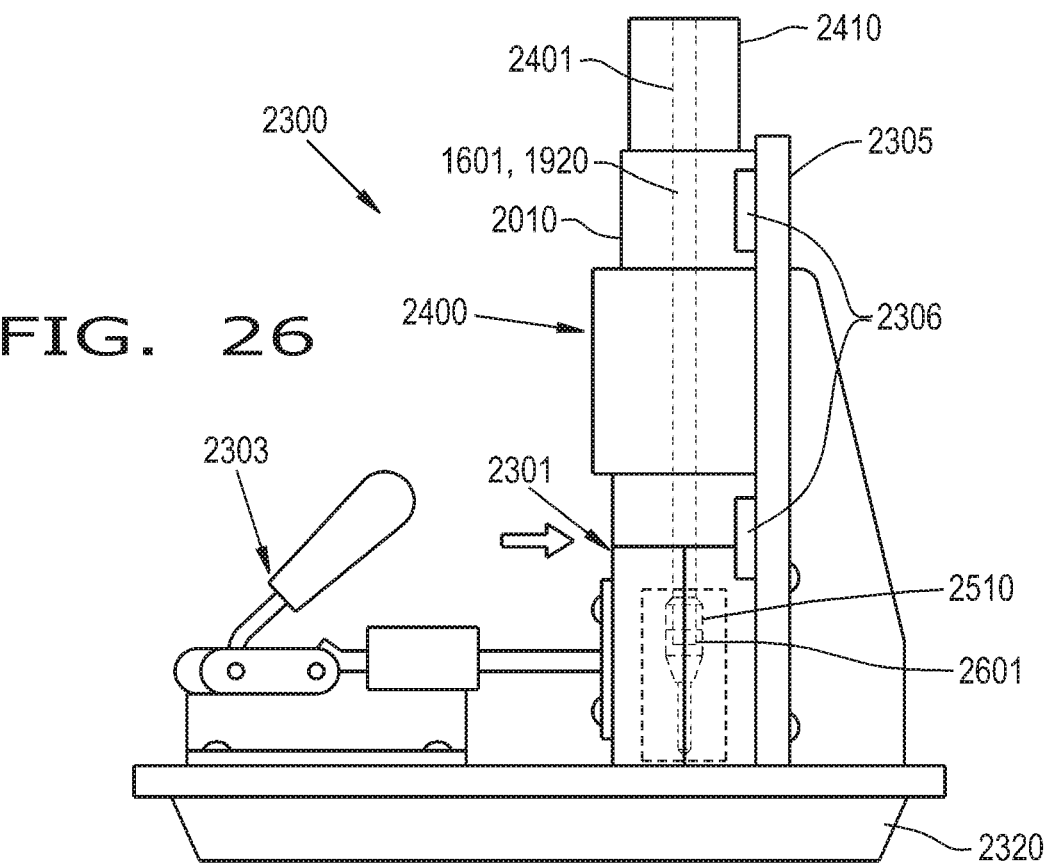
FIG. 26 is a side view of the finishing assembly illustrated in FIG. 25 with another portion of the bound assembly placed in the end fixture and the mold, which has been closed.

Referring specifically now to FIGS. 25-26, an exemplary way of adhering another end fixture 2510, which may include the coupler 14 and surgical cutter 20, to the bound assembly 2400 is illustrated. While the bound assembly 2400 is illustrated in FIGS. 25-26 with the end fixture 2410 already adhered to the first portion 2401 of the flexible coils 1601 and rod 1920, it should be appreciated that the end fixture 2510 may be adhered to the flexible coils 1601 and rod 1920 prior to the end fixture 2410 being adhered. When the end fixture 2510 includes, e.g., the coupler 14 and a drill bit as the surgical cutter 20, the drill bit 20 and coupler 14 may be placed in the opened mold 2301, as shown in FIG. 25. A pre-measured amount of adhesive may be placed in the mold 2301 and a second portion 2601 of the flexible coils 1601 and rod 1920 (illustrated in FIG. 26) opposite the first portion 2401, which has the end fixture 2410 adhered thereto, is placed in the mold 2301 and the end fixture 2510. The mold 2301 is then closed and may be transported by the carousel 2320 to the curing station oven to cure the adhesive in the mold 2301, adhering the end fixture 2510 to the second portion 2601 of the flexible coils 1601 and rod 1920. After the adhesive has cured and the end fixture 2510 is adhered to the second portion 2601 of the flexible coils 1601 and rod 1920, the formed driveshaft may be removed from the mold 2301 and transported to a sterilization and/or packaging station to prepare the driveshaft for delivery and use.

From the foregoing, it should be appreciated that the methods 700, 1800 described herein allow for continuous and rapid manufacturing of flexible driveshafts that may be used in surgical instruments. The methods 700, 1800 described herein are also readily adaptable to automation, reducing the need for manual labor to produce the driveshafts and the labor costs associated with producing the driveshafts. Thus, the methods 700, 1800 provide manufacturing of flexible driveshafts in an economic manner, making it viable for the produced flexible driveshafts to be disposable units to avoid the issues associated with sterilizing and re-using flexible driveshafts in surgical procedures.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims. In addition, this application is intended to cover all combinations of the several embodiments that are consistent with the purpose and functions covered by the overall description within the spirit and scope of the disclosure.

What is claimed is:

1. A method of producing a coil for a flexible drive shaft, the method comprising:
    winding a roving into at least one helical groove of a mandrel;
    coating the roving with an uncured material;
    heating the coated roving to a curing temperature in the at least one helical groove of the mandrel to cure the uncured material and form a composite roving; and
    stripping the composite roving from the mandrel.

2. The method of claim 1, wherein the at least one helical groove extends from a first terminal end of the mandrel to a second terminal end of the mandrel opposite the first terminal end.

3. The method of claim 1, further comprising heating the mandrel to a pre-heat temperature prior to winding the roving into the at least one helical groove.

4. The method of claim 3, wherein the pre-heat temperature is within 20° F. of the curing temperature.

5. The method of claim 1, further comprising dipping the mandrel in a release agent prior to winding the roving into the at least one helical groove.

6. The method of claim 1, wherein the stripping comprises placing a stripping surface next to the at least one helical groove of the mandrel and rotating the mandrel such that the stripping surface strips the composite roving from the mandrel.

7. The method of claim 1, wherein the coated roving is heated in an oven, the method further comprising forcing the mandrel through the oven with an additional mandrel.

8. The method of claim 7, wherein the additional mandrel pushes on the mandrel to force the mandrel through the oven.

9. The method of claim 8, wherein the mandrel and the additional mandrel are linked by a common roving.

10. The method of claim 1, further comprising aligning the mandrel for winding by positioning the mandrel such that an aligner enters the at least one helical groove.

11. The method of claim 1, wherein the mandrel comprises a plurality of non-overlapping helical grooves.

12. A method of forming a flexible driveshaft for a surgical instrument, the method comprising:
    feeding a plurality of flexible coils into a feeder such that each of the plurality of flexible coils are spaced from one another about a rod;
    rotating the rod to wind the plurality of flexible coils about the rod; and
    binding the wound plurality of flexible coils and rod together.

13. The method of claim 12, wherein the rod comprises a flexible material.

14. The method of claim 13, wherein the flexible material comprises at least one of nylon, polyoxymethylene, or a thermoplastic.

15. The method of claim 12, wherein the rod rotates relative to the feeder during rotation.

16. The method of claim 12, wherein the wound plurality of flexible coils and rod are bound together by at least one collet.

17. The method of claim 12, further comprising:
    positioning at least a portion of the bound rod and wound plurality of flexible coils in an end fixture; and
    adhering the end fixture to the bound rod and wound plurality of flexible coils.

18. The method of claim 17, further comprising molding the end fixture in a mold, wherein the end fixture is adhered to the bound rod and wound plurality of flexible coils in the mold.

19. The method of claim 12, wherein the binding comprises binding a plurality of collets to the wound plurality of flexible coils and rod.

20. The method of claim 19, further comprising cutting through the wound plurality of flexible coils and rod in between a pair of adjacent collets of the plurality of collets.

* * * * *